(12) United States Patent
Namespetra et al.

(10) Patent No.: US 7,767,168 B2
(45) Date of Patent: Aug. 3, 2010

(54) SANITIZATION SYSTEM AND SYSTEM COMPONENTS

(75) Inventors: Justin L. Namespetra, Essex (CA); Scott P. Hickey, Niagara Falls (CA); Steve L. Hengsperger, Windsor (CA); Richard S. Zulik, Beamsville (CA); Christopher B. Caldwell, Stoney Creek (CA)

(73) Assignee: Tersano Inc., Oldcastle, Ontario (CA)

( * ) Notice: Subject to any disclaimer, the term of this patent is extended or adjusted under 35 U.S.C. 154(b) by 1278 days.

(21) Appl. No.: 10/875,297

(22) Filed: Jun. 25, 2004

(65) Prior Publication Data

US 2005/0017380 A1    Jan. 27, 2005

Related U.S. Application Data

(63) Continuation-in-part of application No. PCT/CA2004/000042, filed on Jan. 12, 2004, now abandoned.

(60) Provisional application No. 60/482,519, filed on Jun. 26, 2003.

(51) Int. Cl.
*B01J 19/12* (2006.01)
(52) U.S. Cl. .................. 422/186.12; 422/186
(58) Field of Classification Search ............ 422/186.12
See application file for complete search history.

(56) References Cited

U.S. PATENT DOCUMENTS

| | | | |
|---|---|---|---|
| 3,426,513 A * | 2/1969 | Bauer | 55/459.1 |
| 3,775,314 A | 11/1973 | Beitzel et al. | |
| 3,904,362 A | 9/1975 | DiPaolo | |
| 4,123,800 A | 10/1978 | Mazzei | |
| 4,173,051 A | 11/1979 | Reid | |
| 4,290,791 A * | 9/1981 | Matsui et al. | 96/212 |
| 4,306,971 A | 12/1981 | Hankammer | |
| 4,495,043 A * | 1/1985 | Marets | 204/176 |

(Continued)

FOREIGN PATENT DOCUMENTS

JP    5023682 A    2/1993

(Continued)

OTHER PUBLICATIONS

Japanese Patent Application No. 2006-500432, Office Action dated Dec. 3, 2008.

(Continued)

*Primary Examiner*—Jennifer K Michener
*Assistant Examiner*—Xiuyu Tai
(74) *Attorney, Agent, or Firm*—Curtis B. Behmann; Borden Ladner Gervais LLP

(57) ABSTRACT

A multi-use sanitization system is disclosed which includes one or more containers in fluid communication with other system components. Components of the system include an ozone contacting device, such as a vortex-venturi or a sparger, for incorporating ozone into a liquid, an ozone generator to provide ozone to the vortex-venturi, a fluid transfer valve to allow simultaneous flow of liquid into and out of the container, and a pump to promote fluid flow through the system. Optionally, a gas-liquid separator with an optional integral gas release valve, an ozone destructor, an oxidation-reduction potential ozone sensor, or a pour-through type pre-filter may be incorporated into the system.

21 Claims, 20 Drawing Sheets

U.S. PATENT DOCUMENTS

| | | | |
|---|---|---|---|
| 4,931,225 A | | 6/1990 | Cheng |
| 4,969,996 A | | 11/1990 | Hankammer |
| 5,048,404 A | | 9/1991 | Bushnell et al. |
| 5,061,406 A | | 10/1991 | Cheng |
| 5,178,799 A | * | 1/1993 | Brown et al. ............... 261/39.1 |
| 5,218,304 A | * | 6/1993 | Kinlen et al. ............... 324/438 |
| 5,225,078 A | | 7/1993 | Polasky et al. |
| 5,302,325 A | | 4/1994 | Cheng |
| 5,332,494 A | * | 7/1994 | Eden et al. ................ 210/96.1 |
| 5,460,705 A | | 10/1995 | Murphy et al. |
| 5,503,809 A | * | 4/1996 | Coate et al. ............ 422/186.18 |
| 5,690,978 A | | 11/1997 | Yin et al. |
| 5,693,226 A | * | 12/1997 | Kool ......................... 210/541 |
| 5,744,030 A | | 4/1998 | Reid et al. |
| 5,770,033 A | | 6/1998 | Murphy et al. |
| 5,824,243 A | * | 10/1998 | Contreras ................ 261/36.1 |
| 5,846,418 A | * | 12/1998 | Thompson et al. .......... 210/266 |
| 5,851,375 A | | 12/1998 | Bodger et al. |
| 5,863,128 A | | 1/1999 | Mazzei |
| 5,880,378 A | | 3/1999 | Behring, II |
| 5,888,403 A | | 3/1999 | Hayashi |
| 5,893,641 A | | 4/1999 | Garcia |
| 5,927,304 A | | 7/1999 | Wen |
| 5,989,407 A | | 11/1999 | Andrews et al. |
| 6,019,031 A | | 2/2000 | Qin et al. |
| 6,030,586 A | * | 2/2000 | Kuan .................... 422/186.07 |
| 6,086,932 A | | 7/2000 | Gupta |
| 6,093,432 A | | 7/2000 | Mittal et al. |
| 6,103,114 A | | 8/2000 | Tanner et al. |
| 6,135,279 A | | 10/2000 | Dryer |
| 6,171,625 B1 | | 1/2001 | Denvir et al. |
| 6,200,618 B1 | | 3/2001 | Smith et al. |
| 6,238,552 B1 | | 5/2001 | Shannon |
| 6,290,848 B1 | | 9/2001 | Tanner et al. |
| 6,368,472 B1 | * | 4/2002 | McGuire .................... 204/252 |
| 6,379,628 B2 | | 4/2002 | de Jong et al. |
| 6,391,191 B2 | | 5/2002 | Conrad |
| 6,405,875 B1 | | 6/2002 | Cutler |
| 6,485,696 B1 | | 11/2002 | Sato et al. |
| 6,485,769 B2 | | 11/2002 | Audy et al. |
| 6,499,671 B1 | * | 12/2002 | Sands et al. ................ 239/172 |
| 2003/0112012 A1 | | 6/2003 | Mosley et al. |

FOREIGN PATENT DOCUMENTS

| | | |
|---|---|---|
| JP | 8222353 A | 8/1996 |
| JP | 10069962 A | 3/1998 |
| JP | 10230229 A | 9/1998 |
| JP | 2002052301 A | 2/2002 |
| WO | WO 92/16241 | 10/1992 |
| WO | WO 99/48588 | 9/1999 |
| WO | 02/36252 A1 | 5/2002 |
| WO | WO 02/42225 | 5/2002 |
| WO | 0248054 A1 | 6/2002 |

OTHER PUBLICATIONS

Office Action for European Patent Application Serial No. 04701335.4 dated Sep. 30, 2008.

U.S. Appl. No. 10/562,206: Office Action dated Aug. 20, 2009.

European Patent Application No. 04701335.4 Office Action dated Sep. 14, 2009.

* cited by examiner

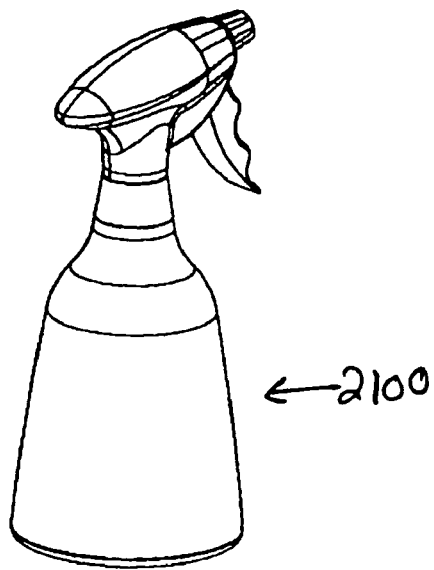
FIG. 21
FIG. 22
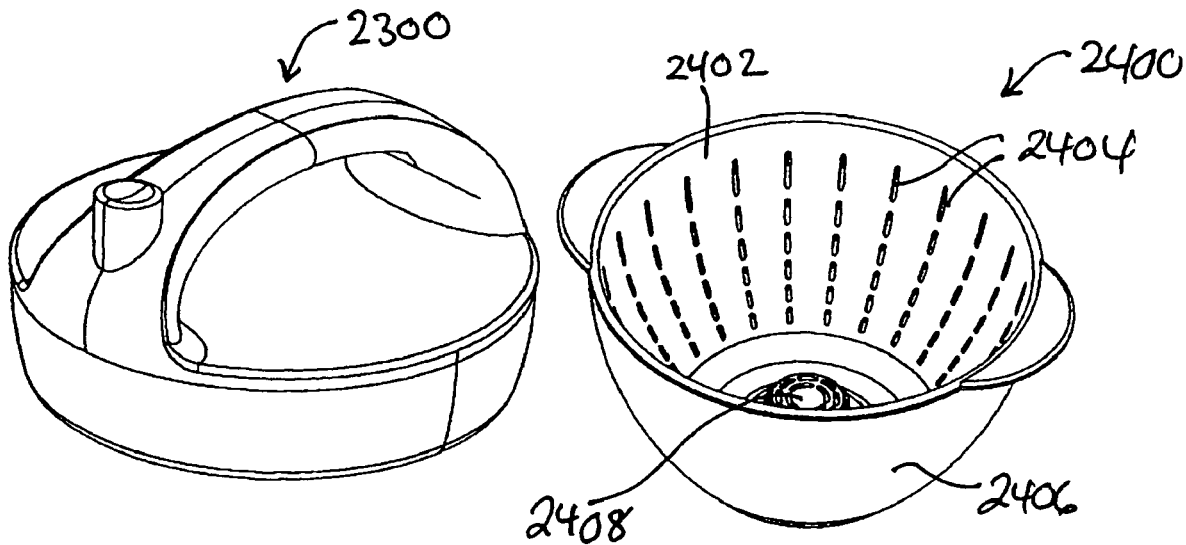
FIG. 23
FIG. 24

SANITIZATION SYSTEM AND SYSTEM COMPONENTS

CROSS-REFERENCE TO RELATED APPLICATIONS

This is a continuation-in-part of International Application PCT/CA2004/000042, with an international filing date of Jan. 12, 2004, published in English under PCT Article 21(2) and now abandoned. This application claims priority to and is entitled to the benefit of U.S. Patent Application 60/482,519 filed Jun. 26, 2003, which is incorporated herein by reference.

FIELD OF THE INVENTION

The present invention relates generally to a sanitization system, as well as to individual components of the system.

BACKGROUND OF THE INVENTION

Microbial contamination is a primary cause of disease. Bacteria and viruses can be found in water, on food and on surfaces. Currently there are several different technologies available to eliminate and/or reduce microbial growth. However, the effectiveness of a particular method depends on the substance being treated and the type of microbe present. Additionally, chemical agents have deleterious effects on human health by themselves or via byproducts generated during the sanitization process.

Harsh chemicals, while capable of sanitizing surfaces, may have persistent smells or corrosive effects on the skin of the user, and would certainly not be acceptable for sanitizing foods.

U.S. Pat. No. 4,173,051 issued to Reid discloses a vegetable washer which uses paddles to agitate and clean the vegetables but has no provision to reduce bacteria.

U.S. Pat. No. 5,927,304 issued to Wen discloses a food washer which uses vibration to remove soil and ultraviolet light to kill bacteria.

There is a need for a sanitization system that allows the sanitization or disinfection with a multitude of applications. There exists a need for a safe method for the consumer to sanitize or disinfect water economically and on site with a single unit. Further, foods, vegetables, plants, and surfaces with which a number of people regularly come into contact would benefit from an effective sanitization system that does not employ dangerous chemical agents.

As used herein, the term sanitization refers to removal of at least a portion of an unwanted component from a substance, such as from a liquid, for example water, or from a solid, for example an object, a surface or a food product. The term purification, when used in reference to water or other liquids, is used synonymously herein with the term sanitization. As used herein, the term disinfection refers to a high level of sanitization of either a liquid or a solid. At the level of disinfection, the vast majority of live bacteria, viruses and/or other "infective" agents are removed from a liquid or a solid. Disinfection is not, however, used synonymously with the term sterilization, which is a high form of sanitization, implying a process more complete than disinfection.

Ozonificadon of Water.

Ozone ($O_3$) is a strong oxidizing agent and is widely used as a disinfectant for food and water. Examples include U.S. Pat. No. 6,171,625 issued to Denvir et al., U.S. Pat. No. 6,200,618 issued to Smith et al., and U.S. Pat. No. 6,485,769 issued to Audy et al. However, these systems are large industrial systems and can not prevent recontamination of the food before delivery to the consumer.

U.S. Pat. No. 6,391,191 issued to Conrad discloses a domestic water treatment appliance which uses ozone to disinfect water.

U.S. Pat. No. 5,460,705 (Murphy et al.); U.S. Pat. No. 5,770,033 (Murphy et al.); and U.S. Pat. No. 5,989,407 (Andrews et al.) disclose devices capable of ozone evolution. The ozone so produced may be used to ozonify water.

Vortex-Venturi Devices.

Prior art documents of interest defining the field of vortex-venturi devices include U.S. Pat. No. 4,123,800 to Mazzei; U.S. Pat. No. 4,931,225 to Cheng; U.S. Pat. No. 5,061,406 to Cheng; U.S. Pat. No. 5,302,325 to Cheng; U.S. Pat. No. 5,863,128 to Mazzei; U.S. Pat. No. 5,880,378 to Behring; and U.S. Pat. No. 5,893,641 to Garcia.

The dispersion of one fluid into another is an important feature of a wide variety of operations. For example, gases are dispersed in liquids for numerous gas dissolving, gas-liquid reaction and gas stripping of dissolved gas applications. Gases are also mixed with gases. Liquids are also dispersed into other liquids for dilution or for liquid-liquid reactions. Examples include the mixing of disinfectants or fertilizers into water.

Many devices have been developed to disperse one fluid (an additive fluid) into another (the main fluid). The purpose of such devices is to bring a proportioned amount of one fluid into contact with another. In addition to this metering of fluid, it may be desired to have the additive fluid well-dissolved and distributed into the main fluid. If the additive fluid is a gas, the efficiency of dissolution is dependent on bubble size and motion. A vigorous motion of small bubbles will accelerate the dissolution of the gas. Vigorous movement will also assist the mixing of liquids.

For example, U.S. Pat. No. 4,931,225 issued to Cheng discloses a method and apparatus for dispersing a gas into a liquid. The gas is injected into the liquid upstream of a venturi. The gas-liquid mixture then flows through the venturi, is accelerated to supersonic speed and then decelerated to subsonic speed. The resulting shockwave breaks-up and disperses the gas bubbles.

U.S. Pat. No. 5,061,406 issued to Cheng discloses a method to disperse a gas into a liquid using an adjustable conical mixer to control the flow of the gas/liquid mixture to a venturi device. The conical mixer creates an annular opening in the venturi and controls the size of the opening. The gas is injected at supersonic speed upstream of the venturi. The gas/liquid mixture is accelerated to supersonic speed and subsequently decelerated to subsonic speed. The resulting shockwaves disperse the gas into the liquid.

U.S. Pat. No. 5,302,325 issued to Cheng discloses a method to disperse a gas into a liquid using a conical mixer. The mixer is placed into a cylindrical pipe resulting in an annular flow. The gas is injected at supersonic speed upstream of the mixer. As the liquid/gas mixture passes through the annular gap it is accelerated to supersonic speed and decelerated to subsonic speed with the resulting shock wave dispersing the gas. The annular flow causes a larger portion of the flow to be supersonic.

These devices have the problem that, while dispersing the gas, they also require additional energy in order to inject the gas.

Venturi based injector-mixers are also known. U.S. Pat. No. 4,123,800 issued to Mazzei discloses a venturi device comprising a constricting section, a throat section, and an expanding section. A plurality of ports are arranged angularly around the inside of the throat section and are interconnected to an annular chamber around the throat section.

U.S. Pat. No. 5,863,128 issued to Mazzei discloses a mixer-injector of the venturi type with a constricting portion, a throat section, and an expanding portion. The injection port is shaped as a continuous groove in the throat section. A plurality of twisting vanes in the constricting portion create a rotary motion to the outer portion of the flow and a plurality of straight vanes in the expanding portion remove some of the rotary motion for improved mixing.

U.S. Pat. No. 5,893,641 issued to Garcia discloses a venturi driven injector comprising a converging portion, a throat portion, and an expanding portion. The secondary (additive) fluid is injected via a plurality of ports arranged radially in a groove near the exit of the expanding portion. The secondary fluid is injected perpendicular to the flow of the main fluid.

Gas-Liquid Separators

The presence of entrained gasses in liquids is frequently encountered and in many cases is not desirable. These include boiler systems and hydraulic systems where the entrained gasses can cause noise or damage components. There are also systems where gasses are entrained purposely. These include the addition of nitrogen into liquids to strip out oxygen. In these systems there is a need to then remove both the entrained gas and the stripped gas and thus supply de-gassed liquid.

Another application of gas-liquid separators is for removing undissolved oxygen or ozone after these gasses have been entrained into water. Ozone is used to disinfect water. Water is capable of dissolving a certain amount of ozone, but most ozonation processes result in a certain amount of undissolved ozone gas. Undissolved ozone is dangerous to release directly into the atmosphere. A method is required to remove and treat the undissolved ozone gas formed as a result of such processes.

Oxidation Reduction Potential (ORP) Sensors.

Oxidation Reduction Potential (ORP) sensors are known in the art, for example, in U.S. Pat. No. 5,218,304 issued to Kinlen et al. and U.S. patent application No. 2003/0112012 by Mosley et al.

U.S. Pat. No. 5,218,304 issued to Kinlen et al. describes a sensor which may be immersed in a fluid to measure the pH and ORP of the fluid. The sensor describe uses a reference electrode of silver-silverchloride and an ORP sensing electrode of a noble metal such as gold or preferably platinum. Disadvantages of using such a reference electrode include cost considerations as well as manufacturing availability for a consumer appliance.

U.S. patent application No. 2003/0112012 by Mosley et al. describes a galvanic probe comprising of a sensor electrode and a reference electrode. The probe uses a reference electrode of a noble metal or antimony or bismuth, optionally an oxide or hydroxide thereof, and an oxidation reduction potential (ORP) sensing electrode of zinc or magnesium, optionally an oxide or hydroxide thereof. The disadvantage of using such a sensing electrode is the cost and manufacturing availability for a consumer appliance.

Sanitization Devices and Processes.

The following U.S. patents relate to disinfection and/or sanitization processes: U.S. Pat. No. 5,851,375 to Bodger, et al.; U.S. Pat. No. 6,379,628 to de Jong, et al.; U.S. Pat. No. 6,019,031 to Qin, et al., U.S. Pat. No. 5,048,404 to Bushnell, et al.; U.S. Pat. No. 5,690,978 to Yin, et al.; U.S. Pat. No. 6,093,432 to Mittal, et al.; and U.S. Pat. No. 6,086,932 to Gupta.

A popular household water filtration device is in the style of a pour-through pitcher. Typically, unfiltered water is added to a basin at the top of the device. Through the action of gravity, water percolates through a filtering media (usually consisting of granulated activated carbon) located between the basin and a collection reservoir. Filtered water is then dispensed from the collection reservoir for drinking. For the general public, gravity-controlled pitcher-type water filtration systems are cost effective. However purified the water produced may be, gravity filtration cannot introduce sanitizing gasses, such as ozone, into the purified water. Further, the purified water so formed may have little sanitizing effect on a surface with which it comes into contact, other than to mobilize or wash away bacteria, viruses or other unwanted substances.

Pour-through style device are unable to filter out and destroy smaller organisms and microbes. To facilitate the flow of water, the filtering media through which water is drawn needs to be of a porous nature. Because of this necessity, such devices do not purify or sanitize water as effectively as other water treatment devices. Part of this inefficiency is caused by a lack of additional purification steps, and reliance solely on the filter itself. Additionally, the filtering media or cartridge used in these pitcher-type pour-through filtering systems usually extends down into the collection reservoir, coming into contact with the filtered water. In some instances, this may be disadvantageous if other methods of liquid purification or sanitization are not employed. The porosity of the filter media may even promote infiltration, collection and growth of organisms. Thus, there is an increased potential for contamination of the filtered water when the filtering media extends into the collection reservoir.

U.S. Pat. No. 5,225,078 issued to Polasky et al., discloses a pour-through gravity-flow pitcher filter.

U.S. Pat. No. 6,103,114 issued to Tanner et al., cites a device which attempts to avoid cross contamination by the design of the spout, pour area and seal between the inner reservoir and the filtered water reservoir. However, the filter in this design still extends into the filtered water reservoir and is a potential source of contamination. U.S. Pat. No. 6,290,848 issued to Tanner et al., discloses a porous particulate filter for removing 99.95% of all 3-4 μm *cryptosporidium* and other protozoan cysts. U.S. Pat. No. 6,103,114, also issued to Tanner et al., describes a carafe-style filter device with a lip over the edge to prevent untreated water from mixing with treated water when pouring.

U.S. Pat. No. 6,391,191 issued to Conrad discloses a domestic water treatment appliance with a pump which uses ozone and a carbon block filter to disinfect water.

U.S. Pat. No. 6,238,552 issued to Shannon discloses a universal insert for a water purifier with a filter on top and bottom, and a guide for sliding the insert into a pitcher.

U.S. Pat. Nos. 4,969,996 and 4,306,971 issued to Hankammer disclose a column-like filter device extending into a collection reservoir. This design may potentially provide a source of contamination.

U.S. Pat. No. 6,405,875 issued to Cutler discloses a carafe-style filter device with an ion-exchange resin and carbon granules which removes 99.9% of all 3-4 μm particles. However, this device extends into filtered water reservoir and thus may be susceptible to contamination.

All references noted herein are incorporated by reference.

Thus, there is a need for improvements in sanitation devices that allow convenient access to purified, sanitized or disinfected water. There is also a need for a system that employs a plurality of technologies to achieve a high level of sanitization. Further a system that allows for purification of liquid in combination with other types of sanitization is desirable if objects, foods or surfaces are to be sanitized with the liquid so formed.

Additionally, there is also a need for an effective sanitization system capable of producing a liquid that can sanitize food, objects and surfaces.

SUMMARY OF THE INVENTION

It is an object of the present invention to obviate or mitigate at least one disadvantage of the prior art sanitization or disinfection systems. Advantageously, the present invention allows the sanitization of a variety of water itself, and any variety of surfaces with which the water so produced comes into contact. Unlike many prior art systems, the present invention is applicable to foods, plants, and surfaces with which food may come into contact. According to an embodiment of the present invention, the system can easily be adapted for use with different treatment containers suited to any variety of applications.

An aspect of the invention provides a sanitization system for producing ozonated liquid, the system comprising: a pump for circulating liquid through the system; a fluid transfer valve for interfacing with a liquid source to be ozonated, allowing simultaneous flow into and out of the system; an ozone generator for forming ozone to be incorporated into the liquid, and an ozone contacting device for incorporating ozone into the liquid.

The ozone contacting device can be a venturi, or a vortex-venturi. The vortex-venturi can include an interior chamber with a central longitudinal axis into which a liquid enters in a direction tangential to the longitudinal axis, the interior chamber of the vortex-venturi having a widened initial section, an narrowed waist section with ozone entry ports formed therein, and a widened mixed fluid outlet section from which ozonated liquid is released, and the ozone generator can be in fluid communication with the vortex-venturi to provide ozone to the ozone entry ports.

The ozone contacting device can include: a sparger disposed in the container and in fluid communication with the fluid transfer valve for incorporating ozone from the ozone generator into the liquid; and an ozone pump in fluid communication with the ozone generator for moving ozone to the sparger.

The liquid source can be contained within a container disposed in fluid communication with the pump. The container can include the fluid transfer valve, and liquid is circulated into and out of the container through the fluid transfer valve. The container can be removable, and a plurality of removable containers having fluid transfer valves disposed therein can be used interchangeably. The pump, the fluid transfer valve, the ozone generator, and the ozone contacting device can be disposed within a base.

The ozone generator can comprises a corona discharge ozone generator. The corona discharge ozone generator can creates ozone using a high voltage/high frequency power supply, the corona discharge ozone generator comprising: an ozone generating chamber having open ends, and a high voltage electrode at each of the open ends; insulating end caps disposed at terminal ends of the chamber, the caps having gas ports formed therein in a direction tangential to the chamber, allowing for vortex flow through the generator; and a ground electrode comprising a metallic foil adhered to a dielectric material.

The system can additionally include an oxidation reduction potential (ORP) sensor in fluid communication with the system for detecting ozone level in the fluid. The system can additionally include a gas-liquid separator downstream of the vortex-venturi for separating undissolved gasses from the ozonated liquid, in which case the system can further additionally include an ozone destructor downstream of and in fluid communication with the gas-liquid separator, for destroying undissolved ozone gas arising from the gas-liquid separator. The gas-liquid separator can separate undissolved ozone gas using centrifugal force, the separator comprising: an inlet through which a gas-liquid mixture arising from the vortex-venturi enters under pressure; a channel following from the inlet; means to force the gas-liquid mixture under pressure into a vortex within the channel so as to generate a centrifugal force to move undissolved ozone gas to the center of the channel and liquid to the perimeter of the channel; a slot positioned around the inside of the channel through which a portion of the liquid is drawn off; an annular chamber in communication with the slot through which the liquid passes; and a gas release valve comprising a gas release port within the channel through which gas exits the channel. The system can additionally include a float for interacting with liquid in the chamber to close the gas release port when the liquid level is high.

The system can additionally include a capacitor-coupled detector of high voltage and high frequency power supply to verify the supply of power to the ozone generator, the capacitor-coupled detector comprising: a first wire contacting a high voltage/high frequency lead to the ozone generator; a second wire in close proximity to the high voltage/high frequency lead to the ozone generator, capacitance being formed due to close proximity of the first wire and the second wire; and a detection circuit in communication with the second wire, for detecting the capacitance comprising a microprocessor and a monostable, to verify a supply of power to the ozone generator. The detection circuit can be powered by an external power source or through said capacitance.

The system can additionally include an oxidation reduction potential sensor comprising: a reference electrode made from silver or plated silver, an ORP sensing electrode made from platinum, plated platinum, gold or plated gold; an ORP sensor in fluid contact with the water path; and a continuously monitoring sensor that controls the process time.

The system can additionally include a pour-through filtration unit. The fluid transfer valve can be a check valve, or a double check valve.

A vortex-venturi according to an embodiment of the present invention for incorporating a gas into a liquid, includes: a cylindrical body with an interior chamber, a liquid inlet, a gas inlet, and a gas-liquid mixture outlet, the interior chamber having a helical path between the liquid inlet and the gas-liquid outlet, the interior chamber comprising a widened initial section decreasing in diameter to form a narrower waist section of a substantially cylindrical configuration, and a widened outlet section expanding to an increasing diameter relative to the waist section, wherein the liquid inlet is tangentially disposed to enter the interior chamber to create a vortex effect of liquid flowing therethrough; and wherein the gas inlet enters interior chamber through entry ports formed in the waist section. The vortex-venturi can have one or more vanes formed in the interior chamber on a surface of the widened outlet section.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

FIG. 21 illustrates a spray bottle that may be used as a container with the system;

FIG. 22 illustrates a carafe that may be used as a container with the system;

FIG. 23 illustrates a reservoir and pad for cleaning surfaces that may be used as a container with system;

FIG. 24 illustrates a strainer and bowl combination that may be used as a container with the system;

DETAILED DESCRIPTION

Figure 1:
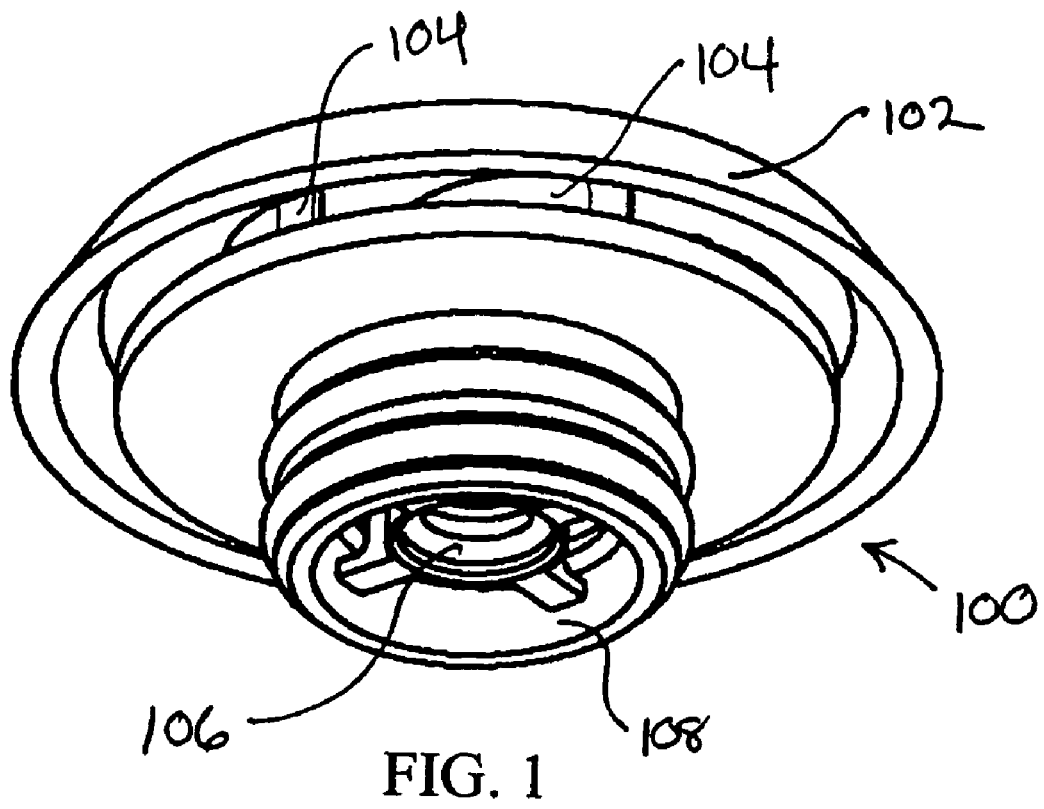
FIG. 1 is an isometric view of an embodiment of a fluid transmission port, implemented as a double check valve assembly.

Generally, the present invention provides a sanitization system and individual components of such a system. The system allows sanitization of a fluid that may then be used to sanitize a wide variety of objects, such as foods or surfaces. Sanitization of an object may be accomplished within the container of the system, or a container holding the sanitized fluid may be removed from the base and transported to an alternative site of use.

A multi-use liquid sanitization system is described herein consisting of a base and at least one removable container. The base comprises a plurality of purification technologies for sanitizing water received from or flowing to the removable container. In particular, a multi-use sanitization system is disclosed which includes one or more containers in fluid communication with other system components. Components of the system include an ozone contacting device, such as a vortex-venturi or a sparger, for incorporating ozone into a liquid, an ozone generator to provide ozone to the vortex-venturi, a fluid transfer valve to allow simultaneous flow of liquid into and out of the container, and a pump to promote fluid flow through the system. Optionally, a gas-liquid separator with an optional integral gas release valve, an ozone destructor, an oxidation-reduction potential ozone sensor, or a pour-through type pre-filter may be incorporated into the system.

A sanitization system producing ozonated liquid according to the invention is described herein. An embodiment of the system comprises a pump for circulating liquid through the system; a double check valve for interfacing with a liquid source to be ozonated, allowing simultaneous flow into and out of the system; an ozone generator for forming ozone to be incorporated into the liquid, and a vortex-venturi for incorporating ozone into liquid. The vortex-venturi comprising an interior chamber with a central longitudinal axis into which a liquid enters in a direction tangential to the longitudinal axis, the interior chamber of the vortex-venturi having a widened initial section, a narrowed waist section with ozone entry ports formed therein, and a widened mixed fluid outlet section from which ozonated liquid is released. The ozone generator is in fluid communication with the vortex-venturi to provide ozone to the ozone entry ports.

Optionally, the liquid source (preferably water) is contained within a container disposed in fluid communication with the pump. The container may incorporate the double check valve in the bottom thereof, and liquid is circulated into and out of the container through the double check valve. Optionally, the container is removable, but it need not necessarily be so. As a further option, a plurality of removable containers having double check valves disposed therein can be used interchangeably.

In this embodiment, the pump, the double check valve, the ozone generator, and the vortex-venturi may be disposed together within a base.

Additional optional components of the system can be added. For example, the system may include an ozone generator, preferably being a corona discharge ozone generator. The corona discharge ozone generator creates ozone using a high voltage/high frequency power supply. In this case, the corona discharge ozone generator comprises an ozone generating chamber having open ends, and a high voltage electrode at each of the open ends; insulating end caps disposed at terminal ends of the chamber, the caps having gas ports formed therein in a direction tangential to the chamber, allowing for vortex flow through the generator; and a ground electrode comprising a metallic foil adhered to a dielectric material.

The system may additionally comprising an oxidation reduction potential (ORP) sensor in fluid communication with the system for detecting ozone level in the fluid.

An ozone destructor may be incorporated into the system downstream of and in fluid communication with the gas-liquid separator, for destroying undissolved ozone gas arising from the gas-liquid separator.

A further optional component is a gas-liquid separator disposed downstream of the vortex-venturi for separating undissolved gasses from the ozonated liquid. When present, the gas-liquid separator separates undissolved ozone gas using centrifugal force. As an exemplary embodiment, the separator may comprise: an inlet through which a gas-liquid mixture arising from the vortex-venturi enters under pressure; a channel following from the inlet; means to force the gas-liquid mixture under pressure into a vortex within the channel so as to generate a centrifugal force to move undissolved ozone gas to the center of the channel and liquid to the perimeter of the channel; a slot positioned around the inside of the channel through which a portion of the liquid is drawn off; an annular chamber in communication with the slot through which the liquid passes; and a gas release valve comprising a gas release port within the channel through which gas exits the channel.

Optionally, the gas-liquid separator may comprise a float for interacting with liquid in the chamber to close the gas release port when the liquid level is high.

The system according to the invention may include a capacitor-coupled detector of high voltage and high frequency power supply to verify the supply of power to the ozone generator. The capacitor-coupled detector can comprise a first wire contacting a high voltage/high frequency lead to the ozone generator; a second wire in close proximity to the high voltage/high frequency lead to the ozone generator, capacitance being formed due to close proximity of the first wire and the second wire; and a detection circuit in communication with the second wire, for detecting the capacitance comprising a microprocessor and a monostable, to verify a supply of power to the ozone generator. The detection circuit may be powered by an external power source or through the capacitance.

The system may additionally comprise an oxidation reduction potential sensor comprising: a reference electrode made from silver or plated silver; an ORP sensing electrode made from platinum, plated platinum, gold or plated gold; an ORP sensor in fluid contact with the water path; and a continuously monitoring sensor that controls the process time.

An embodiment of the invention also pertains to a vortex-venturi for incorporating a gas into a liquid, comprising a cylindrical body with an interior chamber, a liquid inlet, a gas inlet, and a gas-liquid mixture outlet, the interior chamber having a helical path between the liquid inlet and the gas-liquid outlet, the interior chamber comprising a widened initial section decreasing in diameter to form a narrower waist section of a substantially cylindrical configuration, and a widened outlet section expanding to an increasing diameter relative to the waist section. In this embodiment, the liquid inlet is tangentially disposed to enter the interior chamber to create a vortex effect of liquid flowing therethrough; and wherein the gas inlet enters interior chamber through entry ports formed in the waist section.

Optionally, the vortex-venturi may have one or more vanes formed in the interior chamber on a surface of the widened outlet section.

A further embodiment of the invention is a sanitization system for producing ozonated liquid comprising a main pump for circulating liquid through the system; a liquid container; a double check valve within the liquid container for allowing simultaneous flow of liquid into and out of the system; an ozone generator for forming ozone to be incorporated into the liquid, a sparger disposed in the container and in fluid communication with the double check valve for incorporating ozone from the ozone generator into the liquid; and an ozone pump in fluid communication with the ozone generator for moving ozone to the sparger.

The system according to the invention may additionally comprise a pour-through filtration unit as described in more detail hereinbelow.

According to an embodiment of the invention, the base contains a pump, a venturi, a centrifugal degasser, an ozone generator, an ozone destructor, an oxidation reduction potential (ORP) sensor, and appropriate connections and electronics. Various containers can be placed on the base unit depending on what process is required. A pitcher for water sanitization, a container in the form of a bowl and strainer and optionally including a lid, or a sprayer or other container to contain ozonated water to disinfect surfaces may be included. The containers incorporate a double check valve, which interfaces with the base and allows for a single connection point.

According to one embodiment, the base may auto-sense the type of container in place, and thus activates the appropriate program. Alternately, the user can select the appropriate program.

The components of this system are described individually in detail below, along with further description of the sanitization system. Three components which may be used in combination with this system include the double check valve, the vortex-venturi (which may be referred to herein as simply "venturi"), and the ozone generator. Each of these components will be described separately below. Additional optional components can be used, such as a centrifugal gas-liquid separator with integral gas release valve (interchangeably referred to herein as a "degasser"), an ozone destructor, an oxidation reduction potential sensor, or any other component capable of sanitizing a liquid.

Fluid Transfer Valve.

A fluid transfer valve according to an embodiment of the present invention can include any liquid interface, such as a fluid communication port, fluid control port, fluid transmission port, fluid transfer port, and the like. The fluid transfer valve assembly according to the invention allows the control of fluids, and in particular, but not limited to, the control of fluids into and out of a container. The container may be permanently mounted or removable and the flow into and out of the container may occur simultaneously or sequentially.

The fluid transfer valve can be implemented in any number of ways, such as by way of separate check valves for inflow and outflow, for example an influent valve and an effluent valve, or a single double check valve for both inflow and outflow. Check valves are used in a variety of applications where fluid flow needs to be restricted in one direction. Examples include the filling and emptying of tanks and the control of fluid flow in conduits such as pipes. However, if flow is required in two directions simultaneously, for example flow into and out of a tank, two separate check valves are required, and thus two openings are required in the tank.

According to an embodiment of the invention, there is provided a fluid transfer valve, for example a double check valve, which allows two independent flows to occur simultaneously or independently. In the case of the double check valve, these independent flows pass through the same check valve assembly.

The double check valve allows two separate and independent flows to occur through a single check valve assembly. In addition, the device may optionally include a cap capable of diverting flow from one or both of the independent flows, so as to improve flow separation until thorough mixing of fluids from each flow is achieved. Flow diverters, disposed beneath the cap, when present, can impart rotational direction to the fluid flow that passes by. Also, the check valve assembly allows the container to be removed from an interface with the base and prevents the fluid from leaking from either the base or the container when the container is not in place. The two valve stems nested within the check valve assembly can be operated independently or co-operatively.

The double check valve may include a first and second check valve operated independently and having first valve contained (in particular: nested) within the second. Two independent fluid flow paths are thus created, one flowing through the second valve stem and around the first, and a second flow around the second valve stem.

According to one embodiment, the double check valve assembly includes an outer body having an inlet and an outlet with the first and second valve stems contained in the outer body. The outlet of the outer body is the valve seat to the second valve stem. The first valve stem is smaller than the second valve stem, and is contained within the second valve stem and operated along a common axis. The second valve stem has a cylindrical conduit passing through it in which the first valve stem is contained, and also contains the valve seat for the first valve stem. Fluids can thus pass around the first valve stem and through the second. Individual springs surround the first and second valve stems. These springs act on the valves to engage their respective valve seats. The first and second valve stems can be actuated independently or co-operatively.

When the valves are open, two independent fluid flows are created, one flow around the second valve stem and through the outlet in the outer body, and one through the second valve stem and around the first valve stem.

The double check valve assembly according to this embodiment is integral to the wall of a fluid container either permanently mounted or mobile, requiring the control of the input and/or output of a fluid. Different container types for use with the invention are described elsewhere. Preferably, the valve is integral to the lower wall (floor) of the container.

The first valve stem may optional have a cylindrical conduit formed partially through it allowing fluids to pass through the conduit when the first valve stem is unseated from its valve seat.

The outer body may optionally incorporate one or more protrusions that are arranged radially and surround the outlet and the first and second valve stems. These protrusions may take the form of mounting bosses or flow diverters. In the case where the protrusions are flow diverters, these may be configured to impart a rotation motion to the fluid exiting around the second valve stem. In the case where the protrusions are mounting bosses, such mounting bosses are used to mount a removable cap to the outer body and over the first and second valve seats. In such an embodiment, the cap may contains flow diverters, a centrally located conduit and a valve seat.

The cap may be mounted to mounting bosses, in which case the flow diverters contained in the cap create channels through which fluid will flow. The flow diverters may impart a rotation motion to the fluid. When the first and second valve stems are open the second valve stem seats against the valve seat in the cap and the first valve seat passes into the conduit formed through the center of the cap. Thus two flow paths are effectively divided. One flow around the second valve stem, under the cap and through the flow diverters and the other flow through the conduit in the center of the cap and around the first valve stem.

FIG. 1 is an isometric view of an embodiment of a fluid transfer valve implemented as a double check valve assembly (100). The double check valve assembly has a cap (102) disposed on the surface facing the interior of the container in which the assembly is placed. The cap is optional, but when present serves to facilitate mixing within the container. Beneath the cap are fan-shaped blades (104) that promote movement of the water that passes by the blades. The first valve runs through the central axis of the assembly, allowing fluids through in a downward flow. The first valve has a first valve inlet (shown in FIGS. 2 and 3) and a first valve outlet (106). The second valve is formed in an annular configuration around the first valve, and allows return flow (upward) of fluids. The second valve inlet (108) is disposed at the lower end of the assembly, and the second valve outlet is at the upper end of the assembly, beneath the cap, as shown in FIGS. 2 and 3.

Figure 2:
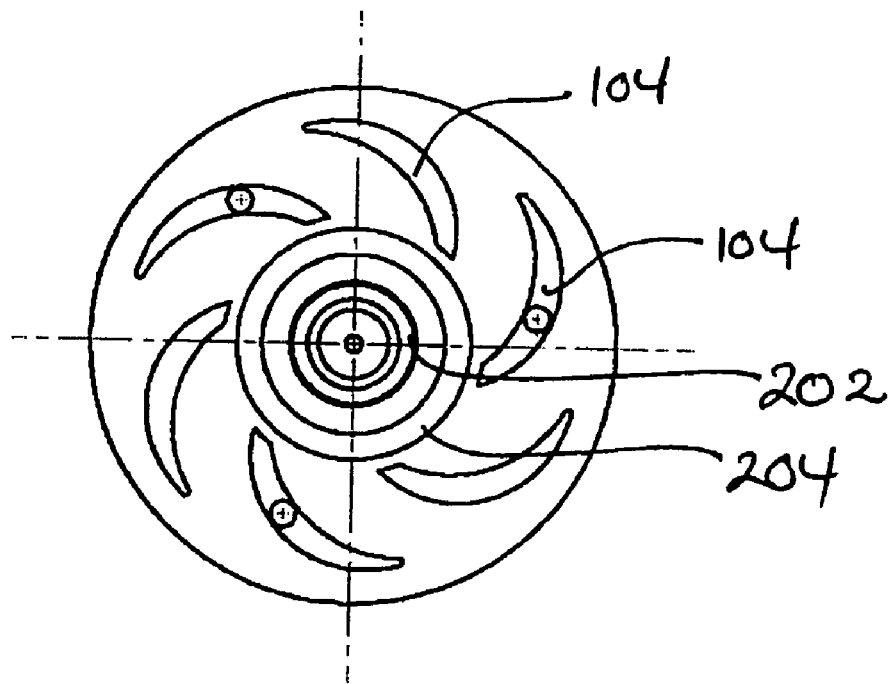
FIG. 2 is a top view of the embodiment of the double check valve assembly shown in FIG. 1, with the cap removed.

FIG. 2 is a top view of an embodiment of the double check valve assembly shown in FIG. 1, with the cap removed. This view more clearly illustrates the fan-shaped blades (104), configured beneath the cap. The first valve inlet (202) and the second valve outlet (204) are visible when the cap is removed.

When the cap is not present, the double check valve retains the same function, but may have less thorough mixing of fluids within the container relative to the embodiment that includes the cap.

Figure 3:
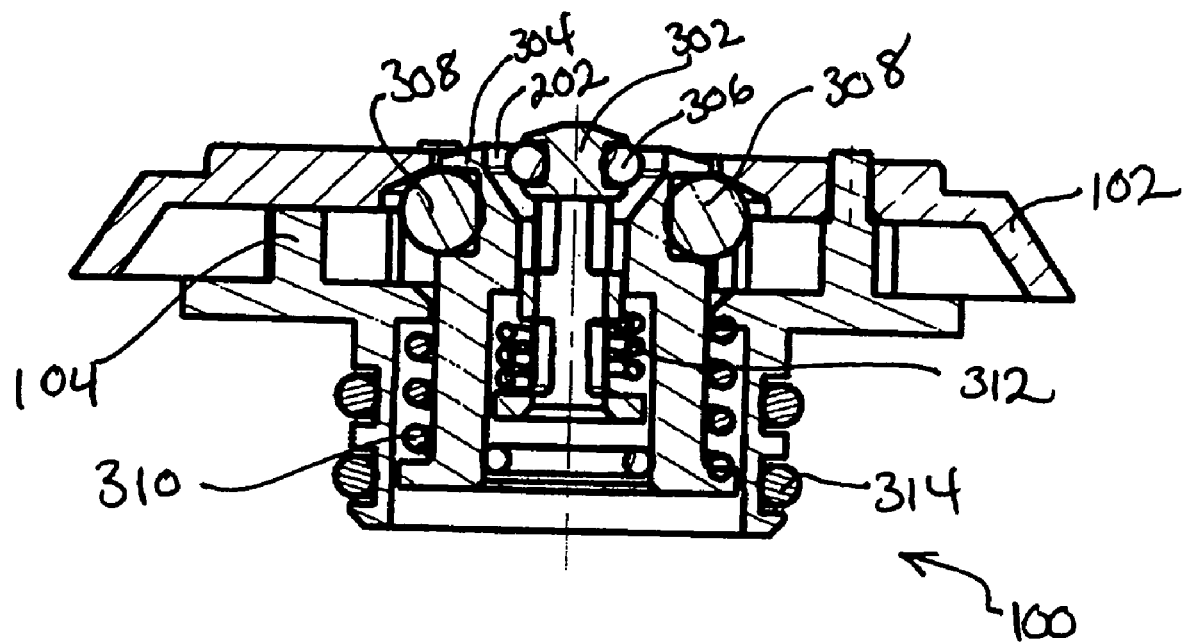
FIG. 3 shows a sectional view of the embodiment of the double check valve assembly of FIG. 1.

FIG. 3 is a sectional view of the double check valve assembly (100). The first check valve stem (302) is shown to be nested within the first check valve inlet (202). The second valve stem (304) is shown outboard of the first check valve inlet (202). A first valve stem o-ring (306) is shown disposed around the first check valve stem. An second valve stem o-ring (308) is shown to encircle the second valve stem. A second valve stem spring (310) is shown, along with an first valve stem spring (312). Outer body o-rings (314) are present on the exterior of the double check valve assembly to allow a sealed (and removable) connection of the assembly with a mating component. In an alternative embodiment, all of the o-rings are removed, and instead dissimilar plastics are used to form seals between the components. This alternative reduces the water left in the reservoir, enabling a design incorporating a shorter reservoir, and the ability to move the position of the screws.

Figure 4:
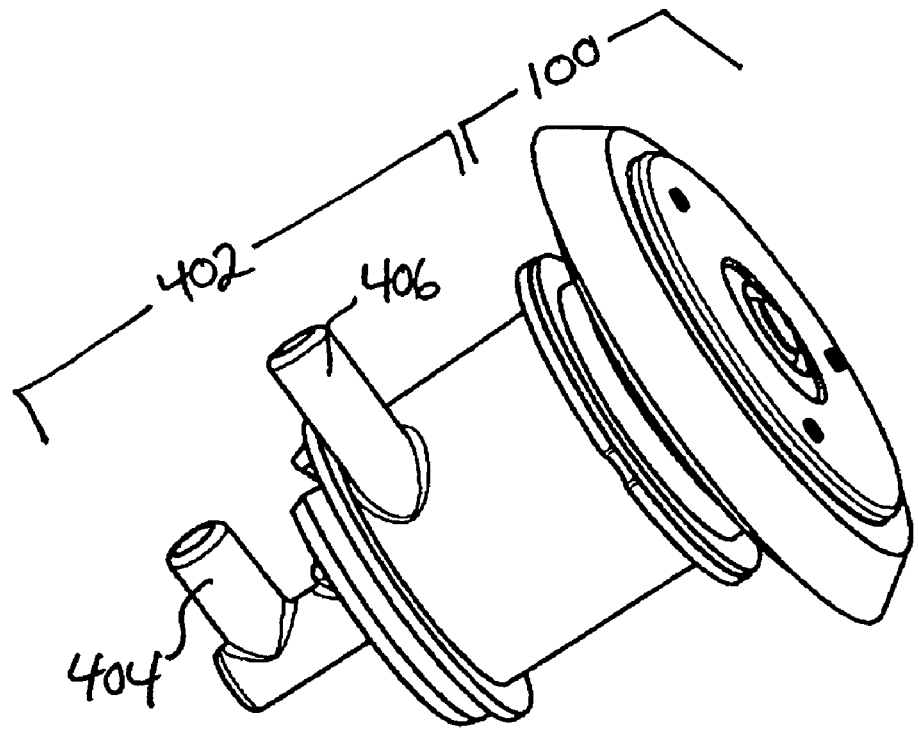
FIG. 4 is an isometric view of double check valve assembly and mating component according to an embodiment of the invention.

FIG. 4 is an isometric view of an embodiment of the double check valve assembly (100) of FIG. 1 and a mating component (402). The mating component comprises a reservoir for fluids from the first and second check valve. A center tube (404) to allow flow of fluid out of the first check valve, while a return flow tube (406) allows fluid to flow into the second check valve. In this embodiment, the double check valve assembly and the mating component are lodged together removably, and the interface between these components is sealed by the outer body o-rings, shown in FIG. 3. Different embodiments do not use a center tube, but another structure is used to perform the same function.

Figure 5:
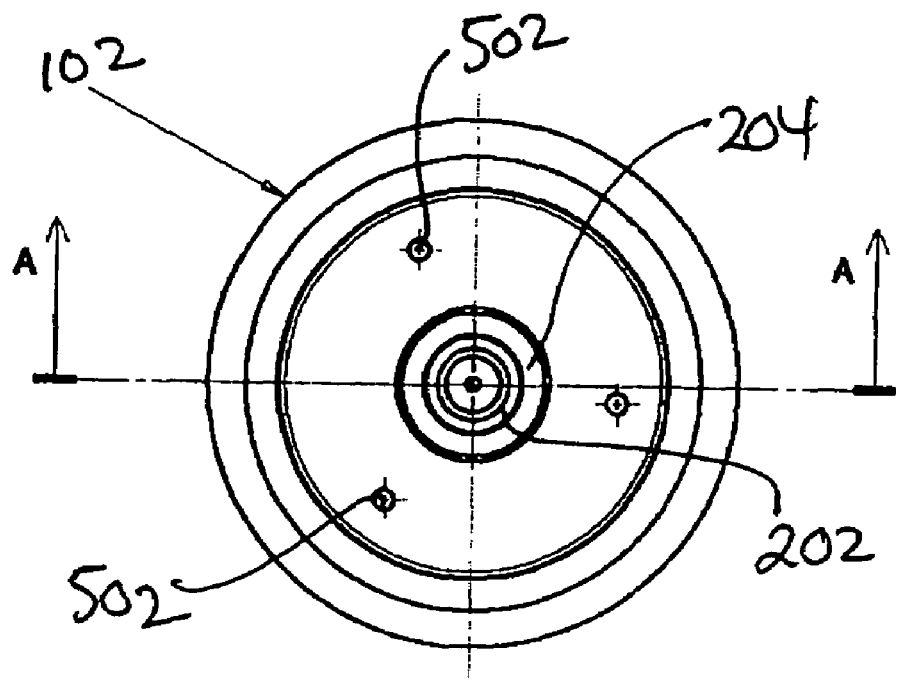
FIG. 5 shows a top view of a cap of the double check valve assembly and mating component according to the embodiment of FIG. 4.

FIG. 5 shows a top view of the double check valve assembly and mating component as shown in FIG. 4. The cap (102) is shown to have the connection points (502) by which the cap is fastened to the fan-shaped blades. The first valve inlet (202) and second valve outlet (204) are shown.

Figure 6:
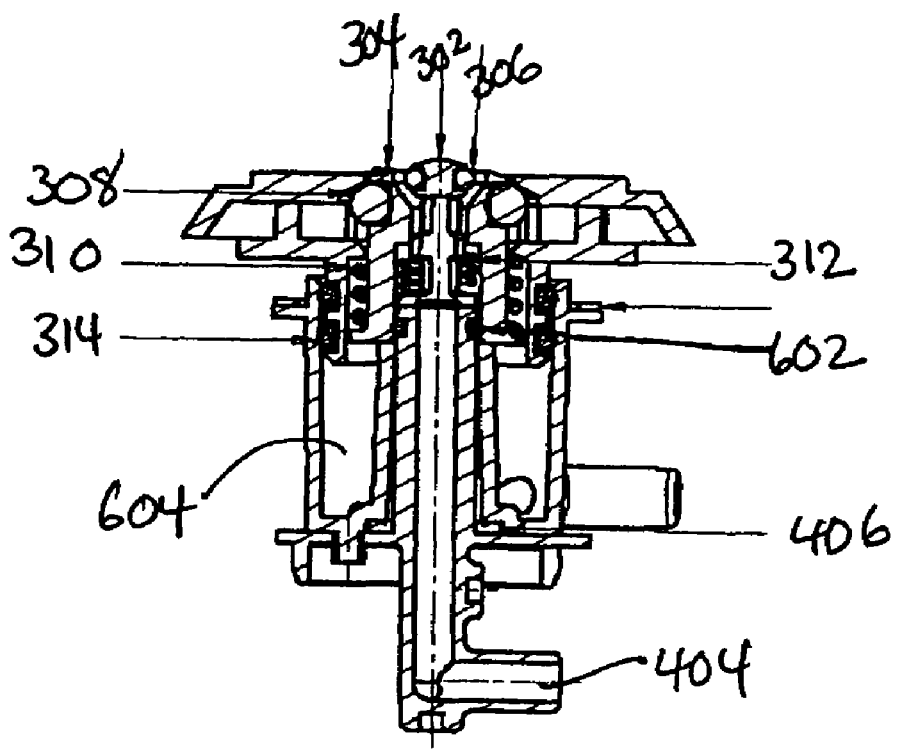
FIG. 6 shows a sectional view of the embodiment of the double check valve assembly and a mating component of FIG. 4, taken through line A-A of FIG. 5.

FIG. 6 is a sectional view of the double check valve assembly and mating component of FIG. 4, taken through line A-A of FIG. 5. The first valve stem (302), the second valve stem (304), the first valve stem o-ring (306), the second valve stem o-ring (308), the second valve stem spring (310), the outer body o-rings (314), and the first valve stem spring (312) are shown. Additionally, a center conduit o-ring (602) is shown, which allows sealing of the double check valve assembly to the mating component. As can be seen in this sectional view, fluid flowing into the first check valve flows through the center tube (404) for further processing, whereas fluid flows through the return flow tube (406) and into a center reservoir (604), while awaiting return through the second check valve. When the double check valve assembly is disconnected to the mating component, the fluid is not allowed to flow upward through the second check valve. Only when the double check valve assembly is mated to the mating component is fluid allowed to flow out of the center reservoir. This advantageously allows fluid to be held back if a container is not in place upon the base.

Figure 7:
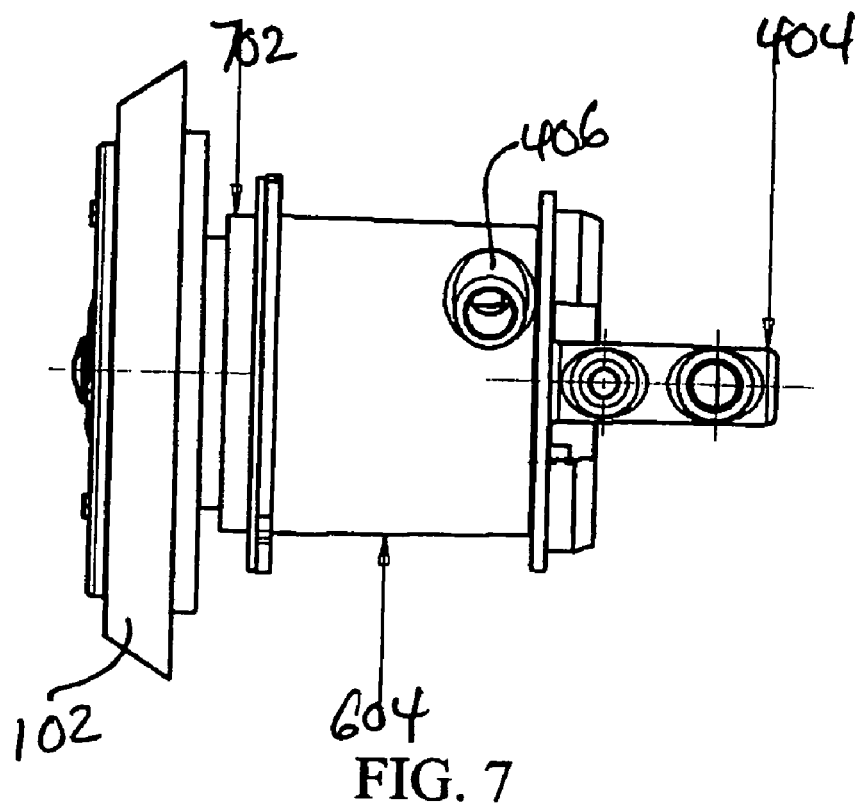
FIG. 7 shows a side view of double check valve assembly and a mating component.

FIG. 7 is a side view of the double check valve assembly and mating component of FIG. 4. The cap (102), center tube (404), return flow tube (406), and central reservoir (604) are shown. In this embodiment, the return flow tube enters from an angled off-set position into the central reservoir, which promotes mixing of fluid in the central reservoir. The top portion (702) of the mating component is indicated, illustrating the region where the double check valve interfaces with the mating component.

Ozone Contacting Device.

The ozone contacting device is an aspect of the present invention that relates to injecting and mixing fluids. The ozone contacting device, or mixing device, is for incorporating ozone into a liquid. The ozone contacting device can be implemented in any number of ways. One implementation of the ozone contacting device is as a venturi, such as a vortex-venturi. Another implementation of the ozone contacting device is as a sparger and ozone pump. In the venturi implementation, this aspect of the invention allows mixing of fluids based on the venturi principle, and in a particular implementation can introduce a vortex component for accelerated entry of a main fluid into the device prior to mixing with an additive fluid. When incorporated into the system of the present invention, the vortex-venturi device can incorporate an additive fluid, such as ozone, into a main fluid, such as water, so as to form ozonated water to be used in further sanitization processes. The ozonated water so formed is also in itself a sanitized product. The device will first be described in terms of its function, and then in terms of its role when incorporated into a sanitization system.

The vortex-venturi device has a main fluid inlet, an additive fluid inlet, and an outlet for the resulting mixed fluid. Between the main fluid inlet and the mixed fluid outlet there is a main fluid inlet channel, a constricting portion of decreasing diameter, a throat, and an expanding portion of increasing diameter. The main fluid inlet is positioned perpendicular to the axis of flow through the outlet, and the main fluid inlet is disposed with an axis tangential to the inlet channel thus forming a high-speed vortex flow. The tangential (or off-set) main fluid inlet is primarily responsible for causing the vortex effect, and the result is a higher speed of flow for the main fluid, and thus improved mixing between the main fluid and the additive fluid.

According to this embodiment, the additive fluid inlet comprising a hollow tube or needle located centrally within the device. The additive fluid inlet extends into the throat portion, and thus forming an annular channel around the inlet. One or more additive fluid outlet ports in the additive fluid inlet injects the additive fluid into the throat portion so as to mix with the main fluid.

The present vortex-venturi device has the advantage that gas (or additive fluid) is dispersed without the need to utilize additional energy to inject the gas. The present invention has the advantage that it uses the venturi effect to draw the additive fluid into the main fluid.

A further advantage of the vortex-venturi device of the present invention is that the tangential entry of the main fluid imparts a rotary motion to the entire flow within the annular channel, and thus creates an annular flow through the additive fluid injection process. This causes a larger portion of the main fluid flow to reach high velocity and a larger portion of the main fluid flow to directly contact the additive fluid. The present invention also allows for the ease of cleaning and the changing of port number, position and sizes, or the needle diameter, thus changing the cross sectional area of the throat.

An embodiment of the ozone contacting device implemented as a vortex-venturi device according to the invention is described below.

According to one embodiment, the vortex-venturi has a cylindrical body with a main fluid inlet, an additive fluid inlet, and an outlet. Between the main fluid inlet and the outlet can be found: a helical main fluid inlet channel, a constricting portion of decreasing diameter which is either frusto-conical or preferably continuously curvilinear in shape, a substantially cylindrical throat portion, and an expanding portion of increasing diameter being frusto-conical in shape.

In this embodiment, the main fluid inlet is positioned perpendicular to the outlet flow axis and tangential to the helical inlet channel thus inducing a high-speed vortex flow. The rotating fluid flow velocity increases as the diameter decreases, thus reducing the static pressure.

The vortex-venturi device according to this embodiment has an additive fluid inlet comprising a centrally located hollow needle extending into the throat portion. Between the needle and throat wall, an annular channel is formed. In this embodiment, the hollow needle terminates in the throat portion, within an outlet port arranged parallel to the outlet flow axis. Alternatively, the hollow needle may extend through the throat portion, terminating in the expanding portion, and having a sharp point at the end. A plurality of outlet ports are formed in the needle perpendicular to the needle axis, and may be located such that the additive fluid is injected in the throat portion.

The additive fluid inlet needle may be formed as part of a separate body, and may be removable from the vortex-venturi device or may be permanently attached or bonded to the rest of the vortex-venturi device. In the case where the additive fluid inlet needle is removable, it may be attachable to the main body via a snap-fit configuration, clips, threads or any other acceptable attachment means. The additive fluid inlet needle may be sealed via o-rings or other such methods, as would be clearly identifiable to one of skill in the art.

The additive fluid inlet body may incorporate a check valve preventing the backflow of the main fluid out of the additive fluid inlet when flow of main fluid is insufficient to create a vacuum.

The removable additive fluid inlet body allows cleaning and/or changing of the additive fluid inlet body, thus allowing the change of needle diameter or port sizes, positions and/or number to vary mix ratios and/or flow rates.

The vortex-venturi device according to an embodiment of the invention may have a plurality of vanes in the expanding portion. These vanes may be positioned parallel to the outlet flow axis and arranged radially. They may interact with the rotating fluid flow to increase mixing efficiency.

Figure 8:
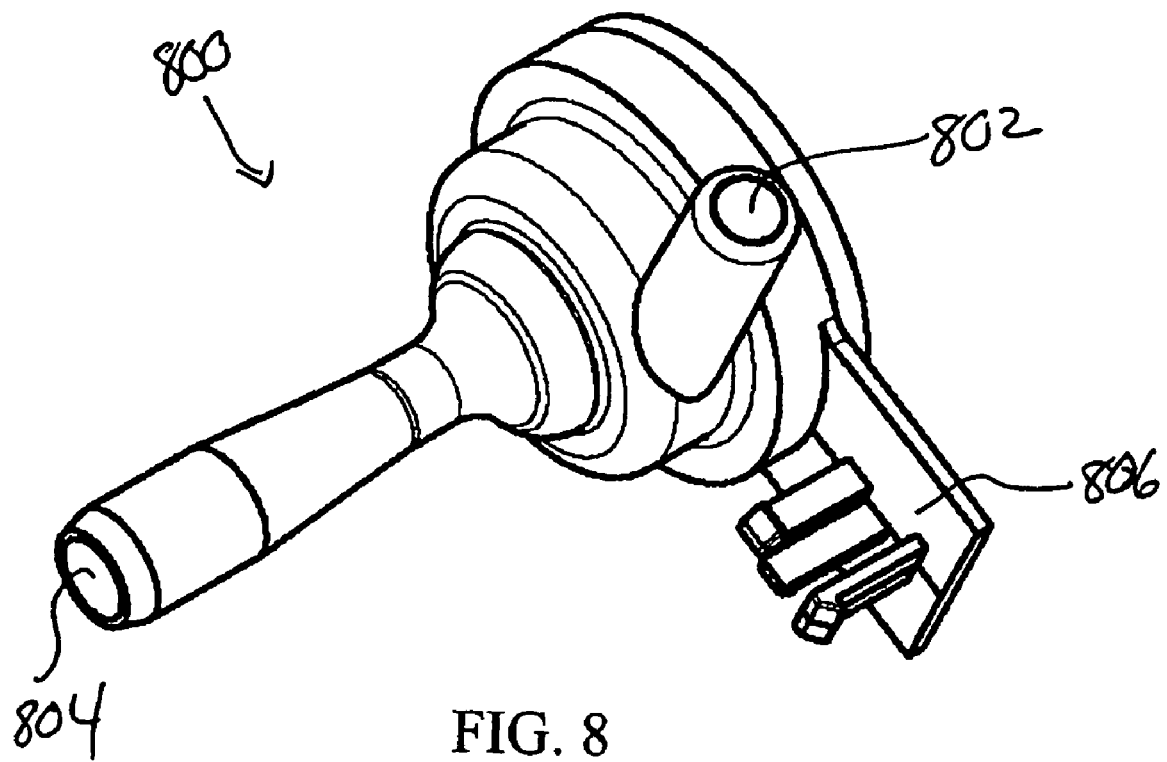
FIG. 8 is an isometric view of an ozone contacting device implemented as a vortex-venturi, according to an embodiment of the invention.

FIG. 8 is an isometric view of a vortex-venturi device (800), according to an embodiment of the invention. Main fluid inlet (802) and mixed fluid outlet (804) are shown. An optional connecting means (806) is illustrated as one possible way in which the vortex-venturi device can be connected to other components, for example, held in place within a sanitization system.

Figure 9:
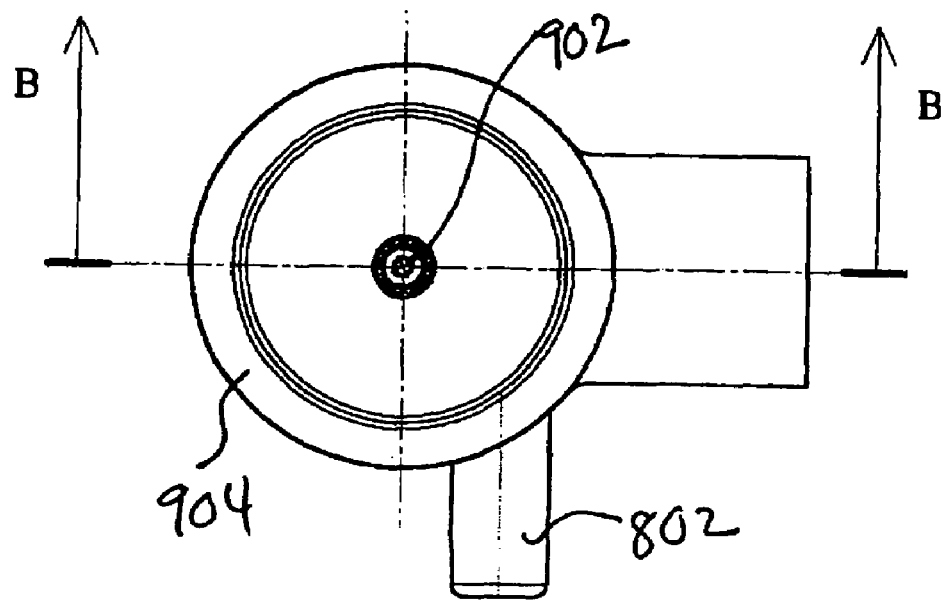
FIG. 9 illustrates an end view of the vortex venturi illustrated in FIG. 8.

FIG. 9 illustrates an end view of a vortex-venturi device according to the embodiment of the invention illustrated in FIG. 8. The additive fluid inlet (902) is illustrated, along with the position of the main fluid inlet (802), which is clearly shown with an axis tangential to the circular shape of the main fluid inlet channel, seen from the exterior as main fluid inlet channel exterior (904).

Figure 10:
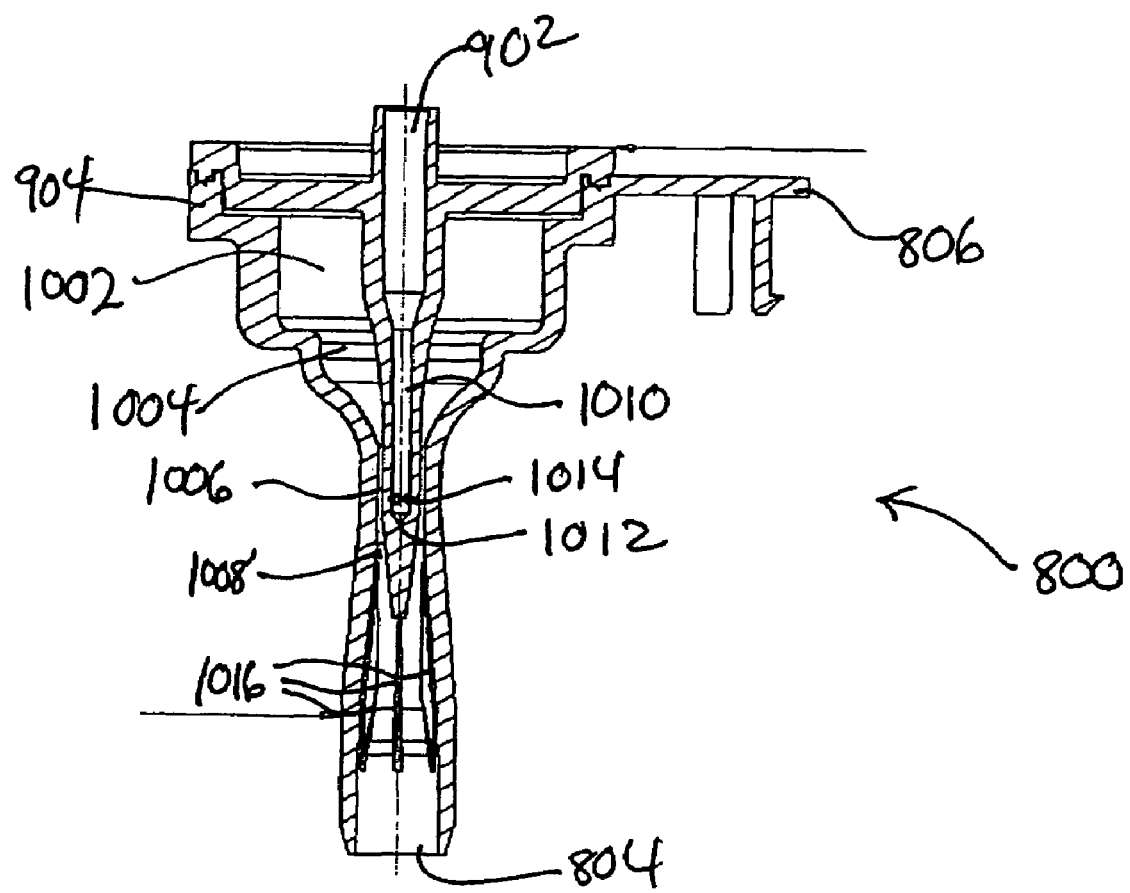
FIG. 10 illustrates a sectional view through the centre of the embodiment of the vortex-venturi shown in FIG. 8, taken through line B-B of FIG. 9.

FIG. 10 illustrates a sectional view through the centre of the embodiment of the vortex-venturi device (800) of FIG. 8, taken through line B-B of FIG. 9. In this illustration, the mixed fluid outlet (804), the connecting means (806), the additive fluid inlet (902), and the main fluid inlet channel exterior (904) are shown. Additionally, the main fluid inlet channel (1002), having a constricting portion (1004), a throat portion (1006), and an expanding portion (1008) is illustrated. A centrally located hollow needle (1010) follows from the additive fluid inlet (902), and terminates in the throat portion (1006) in a sharp end point (1012). A plurality of additive fluid outlet ports (1014), in this case four, two of which are shown, allow injection of the additive fluid into the accelerating main fluid within the throat portion. It is to be understood that a minimum of one additive fluid outlet port is required for the invention, although a plurality of such ports are illustrated in this embodiment. A plurality of vanes (1016) are present in the expanding portion (1008), which interact with the rotating fluid flow, resulting from the vortex effect, so as to increase mixing efficiency of the additive fluid and the main fluid. It is to be understood that vanes are not required in the device, and in the case where one or more vanes are present, a minimum of one vane can be used. In this case, 4 vanes are included, three of which are illustrated here in section. The expanding portion (1008) is configured near the mixed fluid outlet to create a low pressure zone having a vacuum effect that draws the fluids therethrough on the interior of the vortex-venturi device to the mixed fluid outlet (804).

When incorporated into an embodiment of the sanitizing system according to the invention, the vortex-venturi device is located downstream of an ozone generator. The additive fluid intake is thus provided with ozonated air from the upstream ozone generator. The ozonated air is drawn in by the vacuum created within the vortex-venturi device, or alternatively may be provided by a pump to the additive fluid inlet. Water pumped from a container accessed via a double check valve is fed into the main fluid inlet, forms a vortex within the main fluid inlet channel, and the venturi effect draws the water through the constricting portion, causing increased pressure, past the throat portion having additive fluid outlet ports, thereby allowing efficient mixing of ozone and water by high pressure and water acceleration, and further mixing occurs in the expanding portion where the ozone and water interact and mix further. At the mixed fluid outlet, much of the water and ozone has been dissolved into the water, and only a portion of the additive ozone remains as a separate gas. For the remaining ozone gas within this system, a gas-liquid separator having an integral gas release valve can be incorporated to follow downstream of the mixed fluid outlet.

Ozone Generator

The ozone generator incorporated into the system according to the invention is a cost effective apparatus for generating corona discharge. Ozone can be generated by an electrical discharge (such as a "spark") that splits an oxygen molecule into two oxygen atoms. This electrical discharge is also referred to as "corona discharge". These unstable oxygen atoms combine with other oxygen molecules, and the combination forms ozone.

The ozone generator according to an embodiment of the invention is preferably a corona discharge type of ozone generator. The corona discharge ozone generator comprises two cylindrical, insulating end caps, a high voltage electrode, a ground electrode and a dielectric material. The construction of the ozone generator with a wide inner diameter, relative to its length, allows for heat dissipation and hence a consistent output of ozone over time.

The end caps are designed to maintain a consistent air gap between the dielectric and the high voltage electrode. Air enters the end caps tangentially which initiates a vortex action through the ozone generator thus increasing the dwell time between the dielectric and high voltage electrode and increase ozone output efficiency. The end caps have large open ends, closely matching the inner diameter of the high voltage electrode, to allow for heat dissipation during the corona discharge process. Alternately, a fan can be mounted to the end caps to provide convection cooling to the generator. However, due to the wide inner diameter design of the ozone generator allowing heat dissipation, a fan is not necessary.

The end caps are adhered to the ground plane and dielectric using an adhesive.

The dielectric material preferred is a silicon borate glass but other materials such as ceramic or thermoplastics may also be used.

A high voltage electrode constructed from welded or seamless stainless steel tubing of a large inner diameter allows for heat dissipation during the corona discharge process.

According to this embodiment, the ground plane comprises a thin stainless steel foil which is laminated with a high temperature adhesive on one side. This foil is then adhered to the dielectric material (for example, glass) and thus forms the ground plane.

The relative lengths between the ground plane, dielectric material and high voltage electrode are different to eliminate arcing between the components through the end caps.

An alternative configuration of this ozone generator comprises an air pump disposed in fluid communication with the input to the corona discharge ozone generator, for example within the base (when the system incorporates a base). The air pump is used to pump air through the corona discharge ozone generator, thereby ensuring an adequate supply of incoming air. The charged air emerging from the corona discharge ozone generator may then be bubbled into a fluid containers using a sparger or a porous ceramic structure. In this case, the presence of the vortex-venturi is optional, because the ozone becomes incorporated directly into the container. If a plurality of containers are provided, each container houses a sparger and connects fluidly to the base. Of course, a combination of air pump along with a system incorporating the vortex-venturi is encompassed by the system according to the invention.

Figure 11:
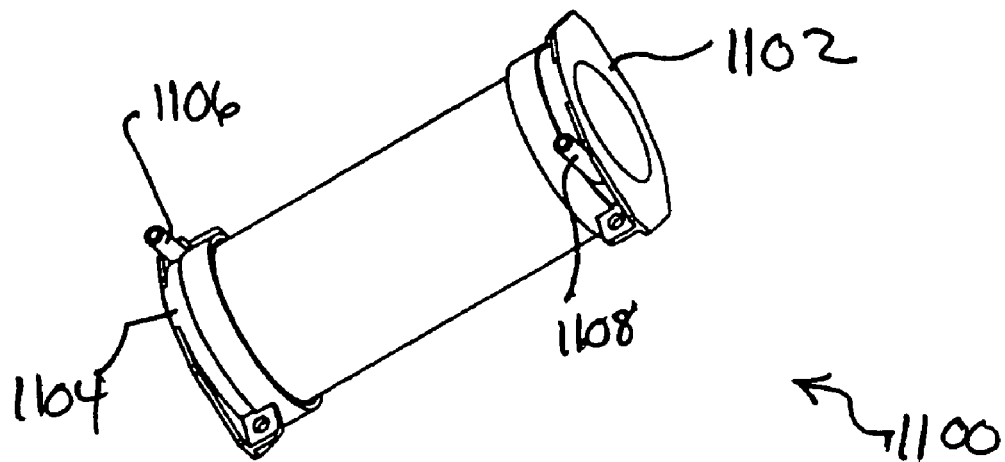
FIG. 11 is an isometric view of the ozone generator according to an embodiment of the invention.

FIG. 11 is an isometric view of the ozone generator (100) according to an embodiment of the invention. End caps (1102, 1104), ozone outlet (1106), and air inlet (1108) are shown. The inlet and outlet are both positioned perpendicularly to the flow axis of gas through the ozone generator, and are both disposed tangentially to the circumference of the ozone generator. In this way, air entering the generator travels a spiral route through the ozone generator and past the electrodes. Thus the spiral route allows the same volume of air to have has more exposure time within the generator, resulting in an enriched quantity of ozone per unit volume of air entering the ozone generator.

Figure 12:
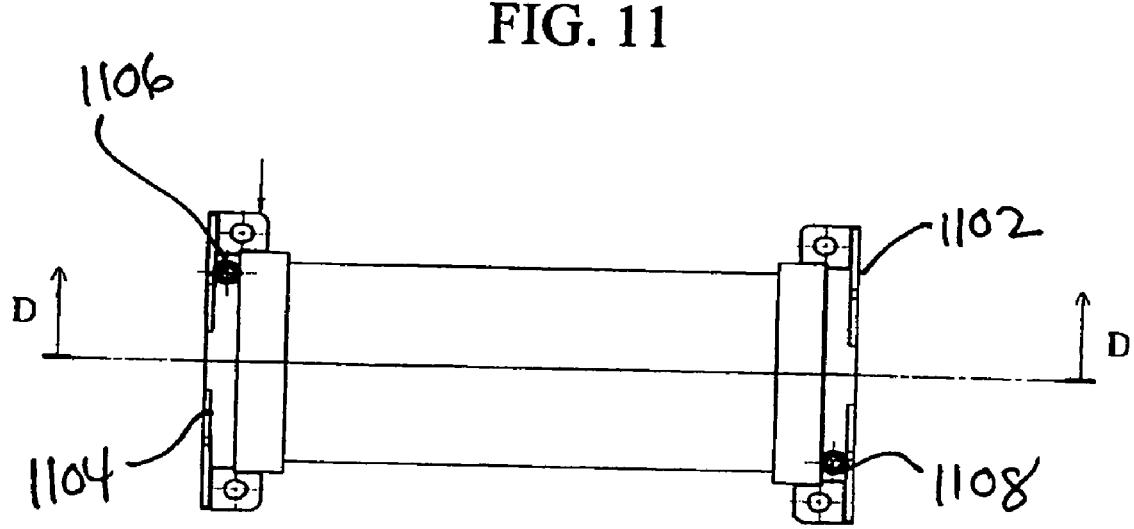
FIG. 12 is a top view of the ozone generator shown in FIG. 11.

FIG. 12 is a top view of the ozone generator shown in FIG. 11. End caps (1102, 1104), ozone outlet (1106), and air inlet (1108) are shown.

Figure 13:
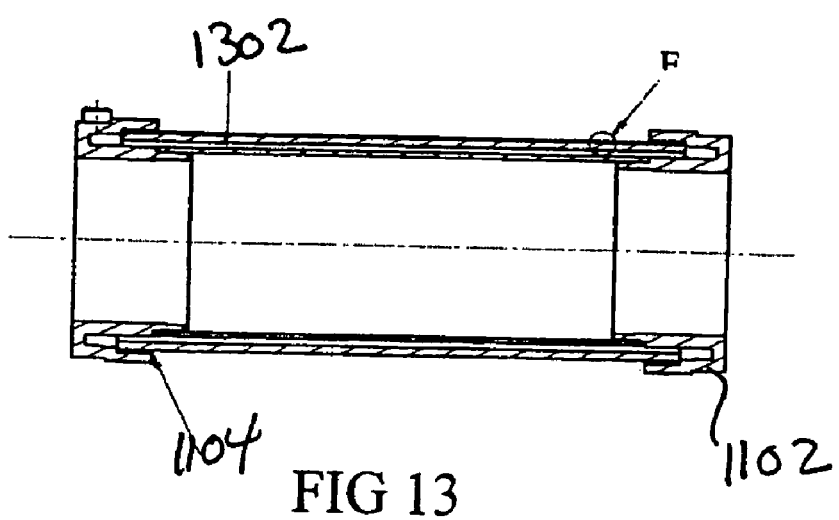
FIG. 13 is a sectional view through the center of the embodiment shown in FIG. 11, taken through line D-D of FIG. 12.

FIG. 13 is a sectional view through the center of the embodiment shown in FIG. 11, taken through line D-D of FIG. 12. The high voltage electrode (1302) is indicated.

Figure 14:
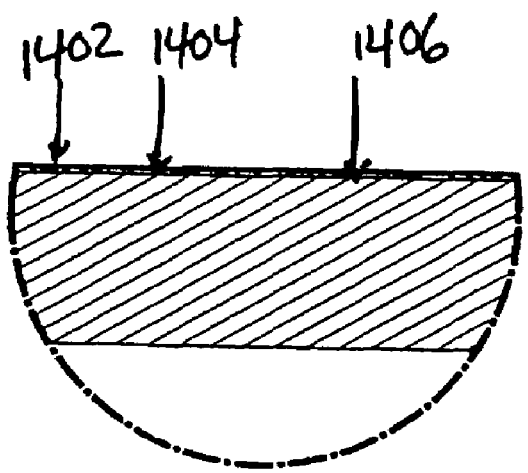
FIG. 14 is a detailed sectional view of the dielectric, adhesive and ground electrode configuration of the ozone generator, taken from detailed section E of FIG. 13.

FIG. 14 is a detailed sectional view of the dielectric, adhesive and ground electrode configuration of the ozone generator, taken from detailed section E of FIG. 13. The ground electrode (1402) in this embodiment, stainless steel foil is shown as the outer-most layer, a high temperature adhesive layer (1404) is disposed beneath the ground electrode, and the dielectric (1406), in this case, a glass tube, is shown just below the adhesive layer. In one example, a typical voltage for the high voltage (inside) electrode is about 4000 V, while the ground (outside) electrode is 0 V.

When incorporated into the system according to the invention, the outlet of the ozone generator is upstream of and in fluid communication with the additive fluid inlet of the vortex-venturi, thereby supplying ozone as the additive fluid through the outlet ports of the centrally located hollow needle.

The remaining components of the system as described hereinbelow are understood to be optional. None of the following components are required to be present for function or operation of the system of the invention. However, according to an embodiment of the invention, each of the components mentioned below are present.

Centrifugal Gas-Liquid Separator with Integral Gas Release Valve.

A centrifugal gas-liquid separator may be used with the embodiment of the sanitization system according to the invention. This separator is interchangeably referred to herein as a "degasser". The separator includes an integrated gas release valve, and allows the removal of entrained gasses from a liquid flow. More specifically, when ozone gas is entrained in a flow of ozonated water, the gaseous ozone can be removed using this separator.

The gas-liquid separator is in fluid communication with the mixed fluid outlet of the vortex-venturi device, so as to allow removal of entrained ozone gas from the ozonated water. The gas liquid separator promotes efficient removal and exhaust of potentially harmful ozone gas, while allowing dissolved ozone to remain in the liquid phase. Thus, formation of degassed ozonated water is accomplished by the system.

According to an embodiment of the invention, a liquid-gas mixture is injected tangentially into a helical channel via the liquid-gas mixture inlet which initiates a high velocity vortex. The vortexing liquid-gas mixture rises up the tube and under centrifugal force the gas is forced to the center of the vortex and the liquid is forced to the periphery. As the liquid-gas mixture rises in the tube, a slot around the tube draws off a portion of the liquid, which is discharged through the liquid outlet. The remaining liquid-gas mixture rises into the valve chamber. The liquid level in the valve chamber interacts with a float that opens and closes a port releasing the gas as needed.

In one embodiment of the invention, a gas-liquid separator incorporates centrifugal force and includes a gas release valve. A liquid-gas mixture enters under pressure through a nozzle and tangentially into a helical channel in the base of the separator. The liquid-gas mixture is forced into a fast turning vortex and rises up the tube. As the vortex rotates, centrifugal force is generated, forcing the lighter gas to the center and the heavier liquid to the outside against the wall of the tube. A slot positioned around the inside of the tube draws off a portion of the liquid and into an annular chamber around the tube and then out the outlet tube. The remaining liquid-gas mixture rises into the valve chamber. A float interacts with the liquid level to either open or close a port. The gas is released from the port in response to the liquid level, thus maintaining pressure in the system.

According to this embodiment, the float may take the shape of a torus allowing the gas to pass through its center while minimally disturbing the vortex motion. Alternately, the float may take the shape of a closed center torus as well as a spherical shape. The float may interact with the port via a lever arm and a seal incorporated into the lever arm. The lever arm multiplies the force of the float (both buoyancy and gravity) to effectively seal the port when the liquid level is high, and to pull the seal away from the port when the liquid level falls. In this case, the lever arm effectively pulls the seal from the port against the internal pressure of the system allowing the gas to escape. Alternately, an electronic float switch may take the place of the float and lever arm and a valve may open and close to expel the air.

The tube of the gas-liquid separator may be either cylindrical or frusto-conical with a diameter increasing from bottom to top.

A cap in the base of the gas-liquid separator, and forming the bottom of the helical channel, can be removable thereby allowing for draining and/or cleaning of the separator. A cap on the valve chamber may incorporate the gas outlet port and the pivot point for the lever arm. This cap is either permanently affixed to the separator or removable for inspection and cleaning of the valve assembly and/or valve chamber.

The cap may incorporate mounts for a baffle. The baffle may have a hole through its center, and aligns with the center axis of the float. The hole allows the gas to pass through the baffle and escape through the port. The hole also allows the arm to connect with the float. When installed, the baffle reduces the chance of fluid escaping out the gas port.

Figure 15:
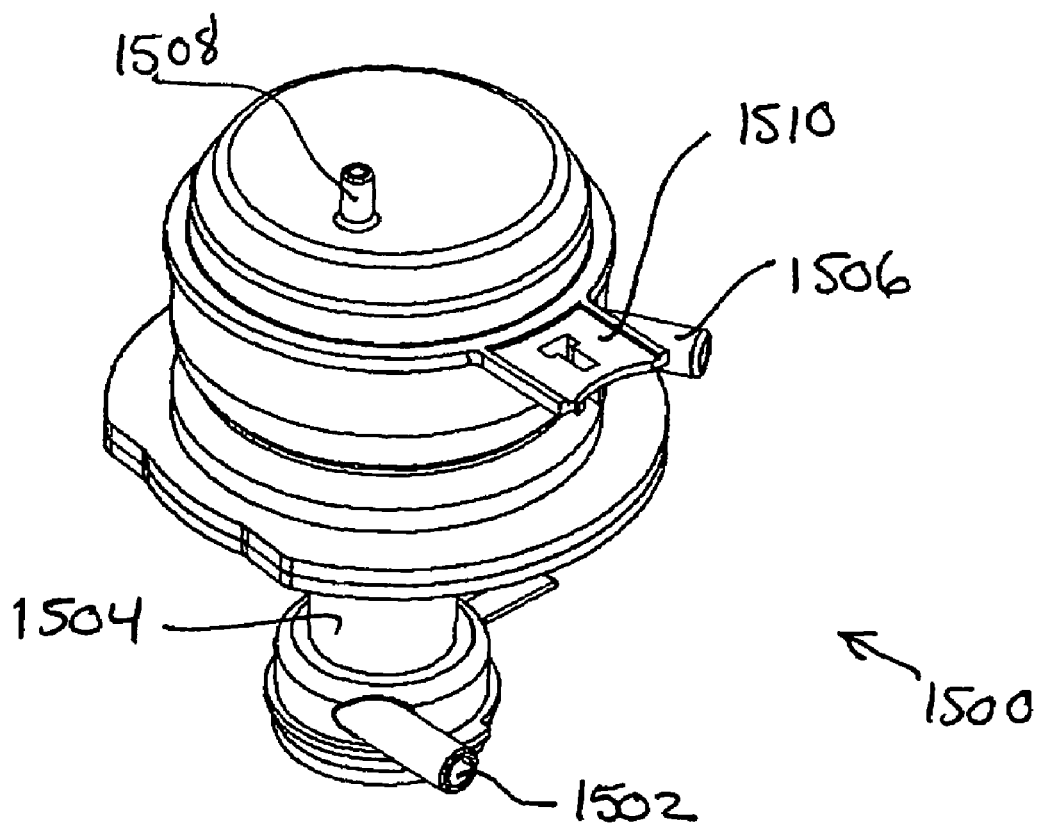
FIG. 15 is an isometric view of a centrifugal gas-liquid separator according to an embodiment of the invention.

FIG. 15 is an isometric view of a centrifugal gas-liquid separator (1500) according to an embodiment of the invention. The liquid-gas mixture inlet (1502) is shown, having a flow axis tangential to the circular channel of the separator. This configuration allows formation of a high velocity vortex. A central tube (1504) is disposed above the inlet, through which the rotating liquid-gas mixture rises. A liquid outlet (1506) is shown disposed above the central tube. A gas outlet (1508) is positioned at the top of the gas-liquid separator. An optional connector (1510) for maintaining the gas-liquid separator in position within a sanitizing system of the invention is illustrated.

Figure 16:
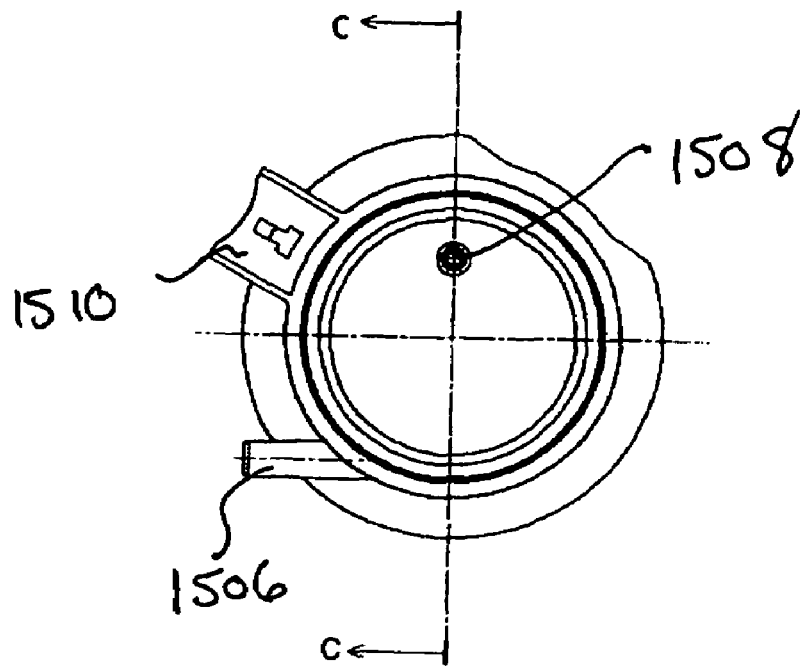
FIG. 16 is a top view of the gas-liquid separator of FIG. 15.

FIG. 16 is a top view of the gas-liquid separator of FIG. 15. Illustrated are the liquid outlet (1506), the gas outlet (1508), and the connector (1510).

Figure 17:
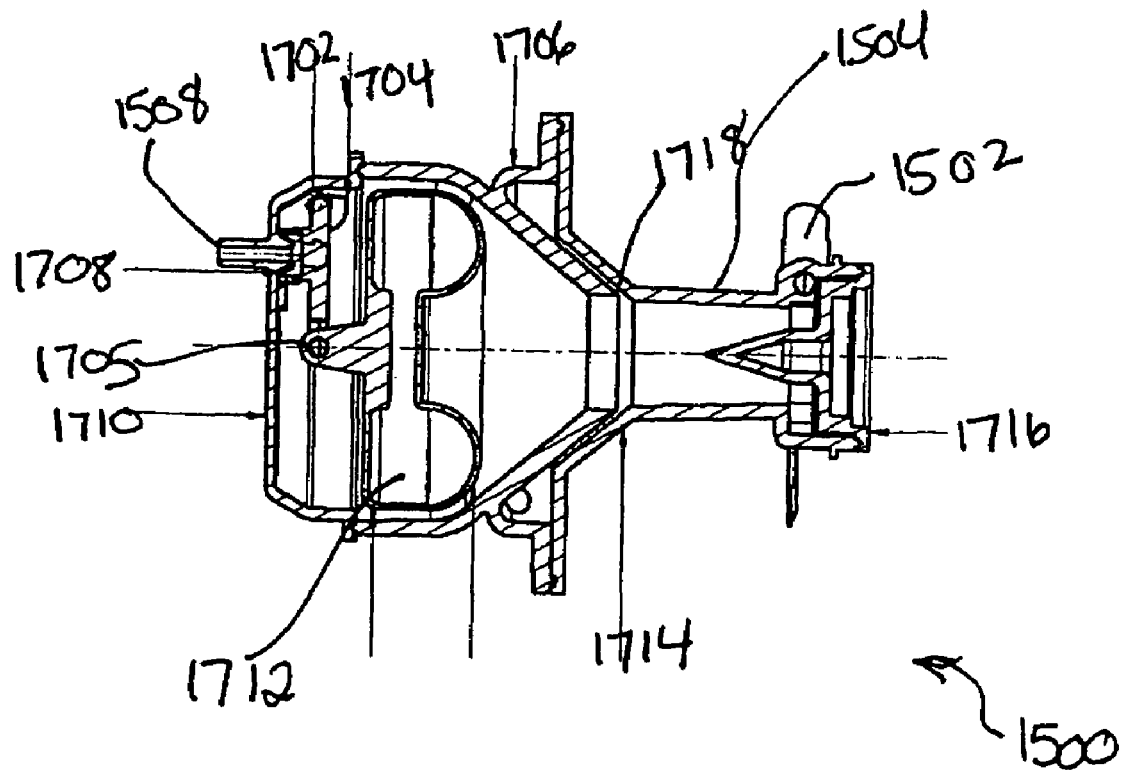
FIG. 17 is a sectional view through the center of the gas-liquid separator of FIG. 15, taken through line C-C of FIG. 16.

FIG. 17 is a sectional view through the center of the gas-liquid separator of FIG. 15, taken through line C-C of FIG. 16. In addition to the liquid-gas mixture inlet (1502), the central tube (1504), the gas outlet (1508), a lever arm (1702), a lever arm retainer (1704), a lever arm pivot point (1705), a valve chamber (1706), a lever arm seal (1708), a valve chamber cap (1710), a float (1712), a vortex tube (1714) and a separator base (1716) are shown. As can be seen in this cross-sectional view, a narrow gap (1718) at the top of the central tube permits liquid to be stripped off between the vortex tube (1714) and the valve chamber (1706).

Although the gas-liquid separator is an optional component of the system, when it is present, certain features have been shown to be beneficial to the embodiment described herein. As used in small-scale systems of the invention, wherein the gas-liquid separator is about 3 to 6 inches in total height (approximately 4 inches), the following dimensions may be used. The narrow gap (1718) may be from 0.01 to 0.1 inches, and preferably from 0.02 to 0.06 inches. The slight step where the narrow gap meets the central tube (1504) is advantageously present, or any type of widening of the tube, extending upwardly is advantageous. The height of the central tube (1504) may be about 1 inch, in an embodiment having a 4 inch total height. However, any height from about 0.5 inches to about 3 inches, for separators ranging from 3 to 6 inches total height (respectively) would be advantageous. Dimensionally, the height of the central tube may be about one quarter of the height of the total separator. The angle of inclination of the central tube can range from 0° (no angle) to about 15°.

The inlet port and the tube of the separator may act as a turbo mixer to help dissolve the ozone into the water. The arrangement wherein the inlet tube is disposed tangentially to the longitudinal axis of the separator, and in which the intake to the inlet is rapid, this effect is achieved, and good mixing results.

As an alternative to a gas-liquid separator, a mixing tube capable of breaking down bubbles in a fluid stream (or "bubble breaker") may be used. A set of mixing tubes with bubble breakers works effectively to dissolve ozone into water, and may be used in place of ozone degassing. The bubble breaker mixing tubes do not vent off the excess ozone, but may be used along in certain jurisdictions in which ozone removal and/or destruction is not necessary.

A Capacitive High Voltage Detector System to Detect Failure of the High Voltage Supply The corona generator relies on a high voltage and high frequency supply of power to generate the ozone required for the embodiment of the invention in which an ozone generator is used. Ensuring that the generator is receiving this supply is beneficial to verify that the unit is functioning properly. A cost effective and reliable sensing system, herein referred to interchangeably as a "high voltage detector", is described, which is able to detect the supply of power to the ozone generator.

The high voltage detector utilizes the fact that the high frequency and high voltage of the supply of power to the ozone generator can feed a usefully large signal to the detector circuit, through a tiny capacitor. This capacitance is created between the high voltage parts and the input to the detection circuit.

Capacitance is created by simply connecting one end of a wire to the input of the detection circuit, and wrapped the other end around the insulated high-voltage feed wire for the ozone generator.

Alternatively, other means of holding the high voltage detector wire in proximity to the high voltage feed wire or other high voltage parts can equally well be used. Other possible arrangements of conductive and insulating parts that create and utilize a capacitance between the high voltage parts and the input to the detection circuit would be apparent to a person skilled in the art, and are encompassed by the invention.

Figure 18:
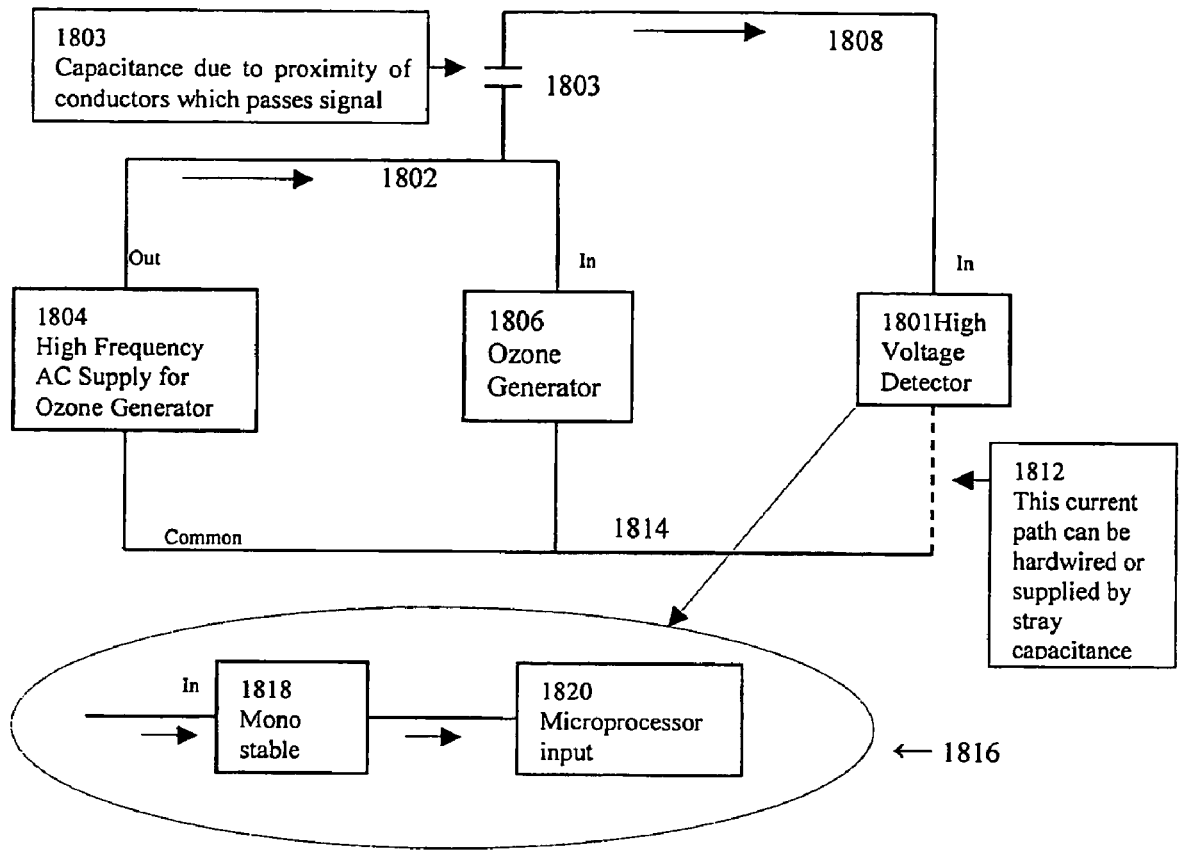
FIG. 18 is a schematic representation of a high voltage detection circuit that may be used according to an embodiment of the invention.

FIG. 18 is a schematic representation of a capacitive pickup (or high voltage detector) circuit that may be used with an embodiment of the invention. Capacitance due to proximity of conductors passes a signal. A high voltage detector is shown, in which the current path (which completes the circuit back to common) may be hardwired or supplied by stray capacitance. The high voltage detector interfaces with a microprocessor for detection of high voltage failure.

As shown in FIG. 18, a high frequency AC supply is provided to the ozone generator. This embodiment of the high voltage detection system (1800) operates as follows. The high voltage feeding the ozone generator is present on an ozone generator feed wire (1802). This wire is connected to the high frequency AC supply (1804) for the ozone generator (1806). A wire (1808) in close proximity to the high voltage feeding the ozone generator is in close proximity to wire (1802) for part of its length. This creates a small capacitance marked as capacitor (1803).

The high frequency and high voltage signal on wire (1802) causes a small current to flow through the capacitor (1803). This current causes a voltage to appear on wire (1808) and at the input of the high voltage detector (1810).

The current path (1812) for the current in wire (1808) is completed by the path (1812) shown as a dotted line connecting to circuit common (1814). This current path can be supplied by stray capacitance or can be supplied by a physical component such as a wire, resistor, capacitor or other form on non-infinite impedance.

The high voltage detector circuit (1810) can be implemented in many ways, which would be understood by those skilled in the art of electrical design. The circuit (1816) illustrating a typical implementation of a high voltage detector, is a monostable flip-flop, which is triggered "on" when voltage appears on wire (1808). The monostable (1818) will revert to the "off" state when it times out, at which point, it would be triggered on again by the signal on wire (1808). The microprocessor (1820) monitors the activity of this flip-flop to verify that it is spending an appropriate portion of time in the "on" state. If the processor detects that the monostable is not "on" for an acceptable percentage of the time, the processor registers a failure of the high voltage supply.

In this embodiment, the system is additionally provided with a detector of the high voltage and high frequency power supply to verify the supply of appropriate power to the corona discharge generator. The detector comprises a wire lead (or "first wire") that is in contact with the high voltage/high frequency lead to the corona generator; a wire lead (or "second wire") that is in close proximity to the high voltage/high frequency lead to the corona generator; and a detection circuit. The detection circuit may be powered either externally or through the capacitance of the detection wire. In this embodiment, capacitance is formed due to close proximity of the first wire and the second wire, The detection circuit is in communication with the second wire, for the purpose of detecting capacitance. The circuit has a microprocessor and a monostable, to verify a supply of power to the corona discharge generator.

An Oxidation Reduction Potential (ORP) Sensor

The processing time of the sanitization system can be controlled either manually or automatically. In the case where automatic control is desired, there is an option to control by either time or by ozone concentration levels in the resulting ozonated water formed. In a preferred embodiment of the system, control of the process is determined by ozone concentration. Thus, a sensor to detect ozonation in water can be incorporated. The sensor can be positioned anywhere within the system of the present invention, provided it is in contact with ozonated fluid.

The sensor described herein is one of any number of sensors that could be incorporated into the system of the invention. In this embodiment, a reference electrode and an ORP sensing electrode are in fluid contact with the sanitization system. The first electrode, being the reference electrode, is formed of silver material. The electrode can be solid silver or plated silver on top of a substrate. The ORP sensing electrode is a noble metal, either platinum or gold, and can be solid platinum or gold, or the metal may be plated on top of a substrate.

In a preferred embodiment, the reference electrode and ORP sensing electrode are plated overtop of stainless steel screws. The screws are then driven into an inlet tube such that the lower portion of each screw is in fluid contact with the water flow through the tube. Lead wires are attached to the screws using terminal lugs. As ozone rich water passes by, an oxidation-reduction potential is generated. This potential is interpreted by standard electronic components of the system, and controls the processing time accordingly.

The screws are readily available for manufacturing in mass quantities, and the plating process for both silver and platinum is well known and widely used by those skilled in the art. The assembly of the sensor is simple, and economical.

Figure 19:
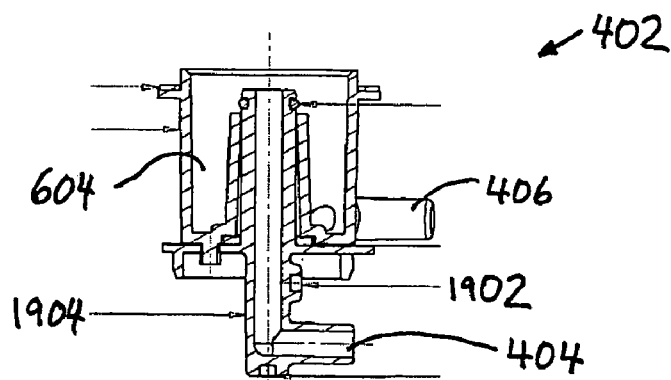
FIG. 19 is a sectional view of an embodiment of an ORP sensor which may be used with an embodiment of the invention.

FIG. 19 illustrates the location and preferred embodiment of the ORP sensor within a mating component (402) of the sanitization system, such as the one shown attached to the double check valve (100) in FIG. 4. The center tube (404), return flow tube (406), and central reservoir (604) are shown. Placement of the electrodes (1902 and 1904) in proximity to the center tube through which fluid enters the system is illustrated.

Gravity-Fed Filter and Other Optional Water Purification Technologies.

The invention may include a gravity-fed filter. In such an embodiment, a gravity-fed filter may be an extruded carbon filter between fabric, a non-extruded carbon filter, or a fabric filter without any activated carbon. The gravity-fed filter may be located upstream of the liquid container, or may be integral to the liquid container in the form of an upper reservoir, dividing the volume of the container into an upper reservoir and a filtered water reservoir. Preferably, the gravity-fed filter does not extend into the water within the filtered water reservoir. However, the system may include a gravity-fed filter that extends downward into a filtered water reservoir, as an alternative to a filter that does not. Such a filter may be in the form of a removable, disposable, and/or rechargeable cartridge.

Additional purification technologies can optionally be used in addition with the system. For example, electrodes; ultra, micro and nanofiltration; an ultraviolet (UV) light source; or additional aeration/oxygenation. The additional purification technologies, if present, are appropriately arranged so as to act on the water as it flows through the system. As an additional purification technology, a pulsed electric field sanitization technology may be used that incorporates electrodes to sanitize or purify water passing therethrough. For example, such a technology is described in Applicant's co-pending International Application No. PCT/CA04/000043 filed Jan. 9, 2004, the content of which is herein incorporated by reference.

The embodiment of the invention involving gravity filtration comprises a container having an upper reservoir for receiving unfiltered water. The upper reservoir has a lower opening; a filtering medium within the lower opening of the upper reservoir for filtering unfiltered water to pass therethrough; and a lower filtered water reservoir for receiving water passed through the filtering medium. The filtered water reservoir has a lower opening that interfaces with the double check valve.

In an embodiment of the invention employing gravity filtration, the container may comprise a pitcher having a flat extruded carbon sheet between fabric as a filter media. The extruded carbon sheet is located in the floor of an upper reservoir. A lid may be provided to cover the upper reservoir. Water received in the upper reservoir slowly filters through the extruded carbon sheet and runs through into lower reservoir of the pitcher. The pitcher may be adapted to sit in a specific location on a base. As a further alternative, an air pump interfacing with the lower reservoir of the pitcher provides air to a sparger medium present in the lower (filtered water) reservoir, thereby releasing bubbles into the water held within the pitcher, allowing further purification of water. In this embodiment, a plastic reflector may be disposed above the sparger medium to aid in circulation of bubbles. In practice, this allows purification of water both by filtration through the extruded carbon filter and by aeration/oxygenation through a pump in communication with the pitcher. A double check valve may be incorporated in this embodiment to ensure that appropriate flow of water into and out of the pitcher is accomplished. Electronic controls may be used within the base to allow detection of the pitcher on the base. Although the extruded carbon filter preferably does not extend below the floor of the upper reservoir, it is to be understood that it is possible to use an extruded carbon filter that extends below the floor of the upper reservoir, and into the water contained in the lower reservoir.

Multi-use Sanitization System.

The system according to the present invention is a multi-use sanitization system having a fluid container, and components allowing ozone formation, ozonation of fluid, and circulation of fluid back into the fluid container. Optionally, other liquid purification technologies may be used in combination with those disclosed herein. Additionally, optional means for removing excess (undissolved) ozone, sensing ozone levels and destroying excess ozone may be employed. The fluid container can optionally be removable. The components may be housed within a base upon which the container is disposed.

According to an embodiment of the invention, components of the system are housed within a base upon which a container may be placed, or with which a container interfaces (in the instance where the container is not removable). These components include a pump, an ozone generator, and a vortex-venturi for incorporating ozone into a main fluid A double check valve for allowing simultaneous flow of liquid into and out of the container is associated with the container, and may have a mating component integral to the base, for the embodiment in which the container is removable. Optionally, a centrifugal gas-liquid separator (or degasser) is included within the base. As a further option, an ozone destructor, an oxidation reduction potential (ORP) sensor, and control electronics may be incorporated.

The container (or plurality of containers) may be either removable or fixed within the system. In the case where the container is integral (and not readily removable) from the system, it may be present in the form of a holding tank. This type of container may be applicable for larger-scale designs where a user would not necessarily require the container to be portable. However, for a small scale or residential applications, it may also be desirable to have a fixed-position, non-removable container from which aliquots of ozonated water can be drawn, for example through a tap, or via a conduit to a select appliance.

According to one embodiment, the system includes a plurality of removable containers. Of course, the system of the invention only requires one container, and it need not be removable. The embodiment in which more than one container is provided, and the containers are removable is discussed hereinbelow. In this embodiment, the control electronics incorporate an auto-sensing circuit, to detect which type of fluid container is connected to the base and to activate an appropriate program. For example, if a fluid container is sensed that is required for drinking water, a lower level of ozonation may be desired. Alternatively, if a fluid container is sensed that may be used for cleaning of surfaces, a higher level of ozonation may be desired.

As an alternative to an auto-sensing circuit, a user may select the appropriate cycle. The treatment period may be controlled manually, or can be set to automatic control based on time and/or ozone concentration in the resulting water. In an embodiment where control is based on ozone concentration, the system can include a sensor to detect the ozone level in the water that is being ozonated, and a means by which to impart the sensed level to the control electronics and optionally convey that information to a display means.

The removable containers incorporate a double check valve in their base, which interfaces with the base unit. This arrangement allows water to flow out of and into the container simultaneously while using a single connection point.

In one embodiment of the invention, when a container is placed on the base, the auto-sensing circuit is activated. The appropriate program (optionally, one specific for that container) is activated and a ready light is illuminated. The user then activates the process by pressing a button. The pump draws water from the container and pumps it through a venturi. The venturi has a gas inlet that draws in ozone-enriched air derived from the ozone generator. The ozone generator may be a corona-discharge type, and converts a portion of the oxygen in the air into ozone, or may be any other acceptable type. The ozone is mixed with the water in the vortex-venturi to make ozonated water. The ozonated water then passes into a centrifugal liquid-gas separator, which removes undissolved gasses, such as air and undissolved ozone, while leaving dissolved gasses present in the ozonated water. The removed gas may be is directed to an ozone destructor, which converts ozone into oxygen and safely releases it into the atmosphere.

Alternatively, the liquid-gas separator may direct expelled gas back into the inlet of the venturi to be re-dissolved into the water or equally effective by directing the expelled gas into the inlet of the ozone generator. The ozonated water leaves the liquid-gas separator and is directed back into the fluid container. The cycle continues until a predetermined time and/or ozone concentration is reached. An ORP sensor is located at the inlet of the system which continuously monitors the level of ozone in the water and controls the process cycle of the unit.

As a further alternative to re-dissolving gasses expelled from the gas-liquid separator, it is optional in certain jurisdictions to release such expelled gasses (oxone-containing) to the atmosphere. Thus, in jurisdictions were regulations permit, neither the recycling of ozone-containing expelled gasses nor the destruction of ozone are necessary. In North America, regulations exist to determine acceptable levels of expelled ozone.

When the process is complete, communication is made to the user via a light and/or audible alarm indicating that the container can be removed.

Each container may incorporate a double check valve in its base, which interfaces with a receptacle in the system base, and allows the container to be removed without leaking. The check valve allows water to flow out of and back into the container without requiring additional connections. Water from the container flows out by a pump or other means, through the venturi, through the degasser and back into the container. The process continues until the preset time and/or ozone concentration is reached. Ozone is generated in an ozone generator and mixed with the water in the venturi. The liquid-gas separator removes undissolved ozone as well as entrained air. The ozone removed by the liquid-gas separator is dissociated by the ozone destructor and safely released into the atmosphere.

Optionally, a container may take the form of a water pitcher for potable water sanitization. The container may also take the form of a bowl and strainer for sanitizing fruits and vegetables. Alternatively, the container may take the form of a spray bottle to contain ozonated water to be applied to surfaces, or of a reservoir and pad for cleaning surfaces. The container may also take the form of an inner and outer container for sanitizing small objects such as dentures, infant pacifiers etc. Also, the container may be a decanter to contain ozonated water when a larger quantity is required. Examples include pouring over foods such as meat, to rinse utensils or hands.

The sanitization system has a variety of applications both in residential and personal use, and for industrial and/or medical use. Examples of these include: preparation of purified drinking water or formation of ozonated drinking water for sanitization of objects or surfaces. Ozonated water formed with the sanitization system may be used to treat medical conditions, such as acne (having bacterial-related origins), foot fungus, sanitization of cuts, topical medical treatments for skin, cleaning of medical devices. Industrial uses for the food preparation industry may employ ozonated water formed according to the invention. For example, commercial use in cleaning surfaces in restaurants, food processing plants (such as meat processing plants), food packaging plants, such as factories, in supermarkets where produce is required to be kept fresh. Shelf-life of fresh produce may be extended by periodic spraying with ozonated water formed according to the invention. Employees may benefit from access to ozonated water for hand-washing in an industrial or public setting. Plants and flowers may be sprayed or watered with ozonated water formed according to the invention.

For home use, vegetables and fruits may be rinsed in container in the form of a strainer attached to the base. For oral care, ozonated water so formed can be used to clean teeth, toothbrushes, or as a mouth rinse. Home wound care could incorporate the ozonated water in lieu of stronger solvents such as rubbing alcohol or hydrogen peroxide. As a deodorizer, the ozonated water so formed can be used to spray surfaces or interior surfaces, such as shoes.

Additionally, for home use, the system can be installed either as a counter-top model, or as an upstream built-in unit supplying water to home appliances. By using ozonated water for clothes washing or dish washing, the amount of detergent required can be reduced or eliminated.

Many other industrial and residential applications can be envisaged by one of skill in the art, and these fall within the scope of the invention.

Figure 20:
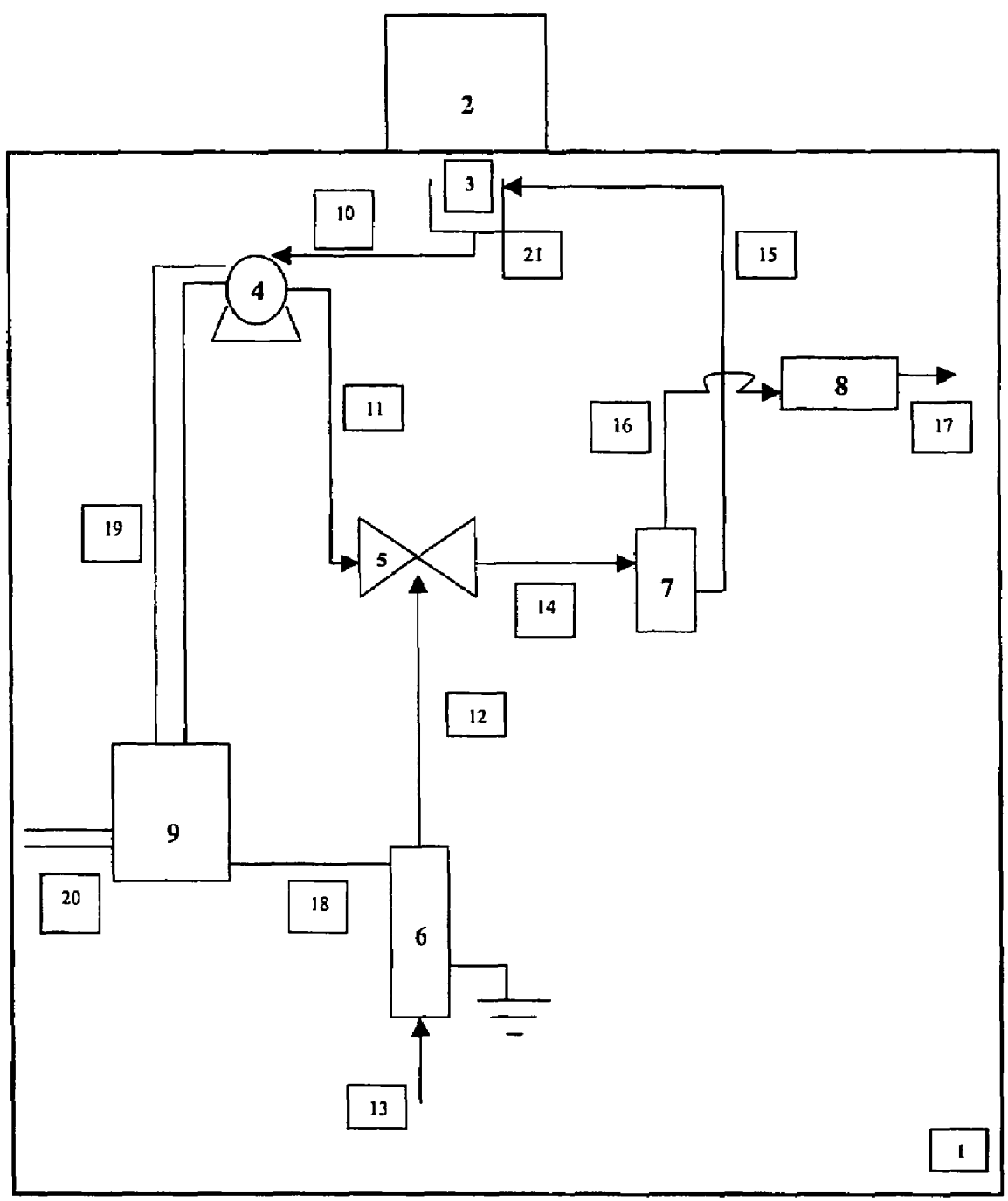
FIG. 20 is a schematic diagram of an embodiment of the system according to the invention.

FIG. 20 is a schematic diagram of an embodiment of the multi-use sanitization system according to the invention. FIG. 20 shows a base (1), and a removable container (2). The treatment container incorporates a double check valve (3) which allows water to flow into and out of the container via a single connection. When the container is placed on base the double check valve interfaces with a socket (21). An autosensing circuit incorporated in the electronics (9) activates an appropriate program to commence the ozonification process.

Power is supplied by 115V AC through wires (20). The electronics convert the main power into 12V DC to be supplied to the pump (4) via wires (19), and to high voltage AC for the ozone generator (6) via a wire (18).

When the system is active, water is drawn from the container, through the double-check valve into the socket and through a conduit (10) into the pump. The water then flows through a conduit (11) and enters a vortex-venturi (5). As the water flows through the vortex-venturi, it generates a vacuum which draws air into the ozone generator through an input (13) and into the vortex-venturi via a tube (12). The ozone generator is a corona discharge type, which converts a portion of the oxygen in the air into ozone.

The water with bubbles containing ozone and air leaves the venturi via conduit (14) and enters the centrifugal gas-liquid separator (7). Centrifugal force generated within the gas-liquid separator forces any air and undissolved ozone out of the water. The extracted gas is directed to an ozone destructor (8) via tube (16). The destructor contains preferably a CARULITE™ catalyst (CARULITE is a registered trademark of the Carus Corp. of Peru, Ill.) which dissociates the ozone into oxygen and safely releases it to the atmosphere (17).

The water now containing dissolved ozone is directed back into the container (2) through the double check valve via a conduit (15) and socket (21). The process continues until the program is completed.

FIG. 21 illustrates a spray bottle (2100) that may be used as a container with the system.

FIG. 22 illustrates a carafe (2200) that may be used as a container with the system.

FIG. 23 illustrates a reservoir and pad (2300) for cleaning surfaces that may be used as a container with system.

FIG. 24 illustrates a strainer and bowl combination (2400) that may be used as a container with the system. The strainer (2402) is shown as the internal portion of the container, having openings therein (2404) for liquid to pass through and into the bowl (2406), which is shown as the external portion of the container. A liquid interface (2408) can be seen at the bottom of the container through which water flows in order to enter and exit the container. This interface is in fluid communication with the double check valve, disposed on the bottom of the container (not shown). The container can optionally include a lid (not shown). The lid itself can define or have openings therein, to produce a lid strainer, which can be removably attached to the bowl, by mating components, a locking mechanism, or any other suitable means. The use of such a strainer lid is beneficial in straining the water back out of the container after purification or sanitization of the items in the container, without having to remove the strainer from the bowl.

Figure 25:
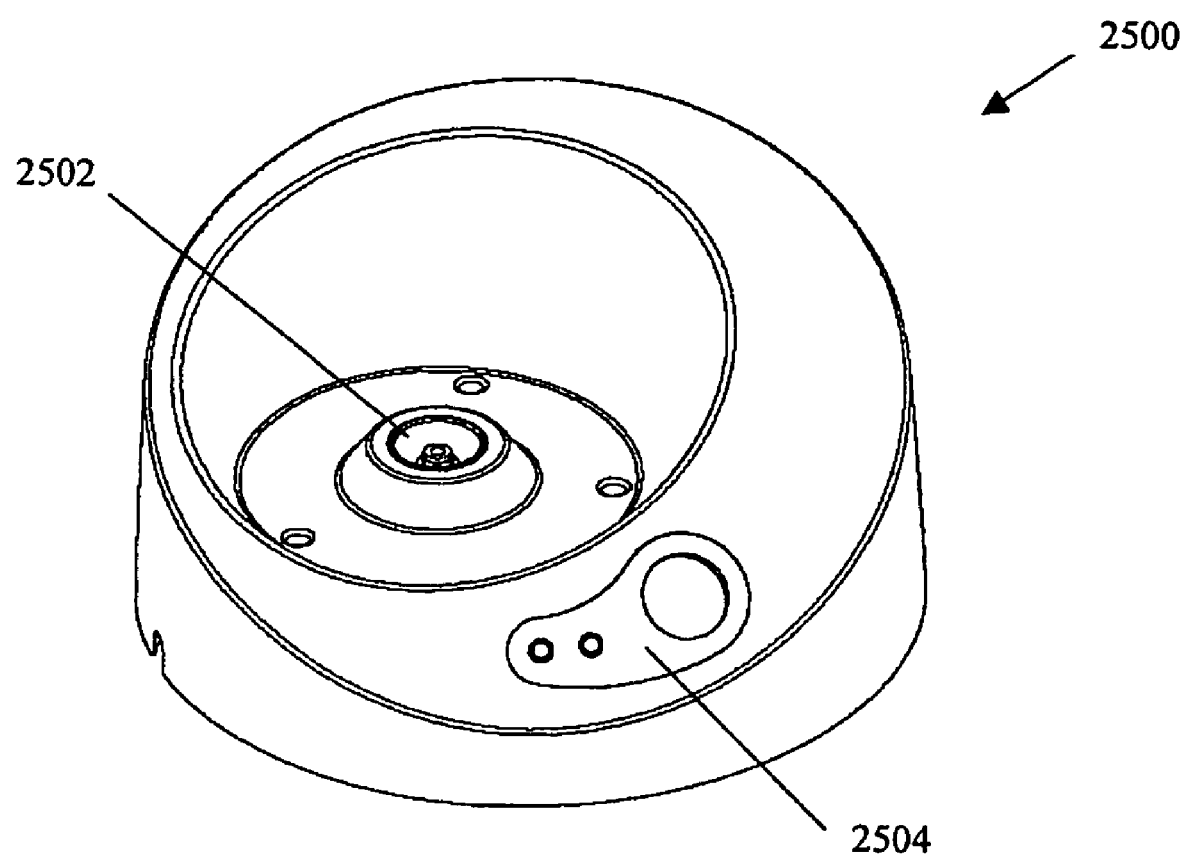
FIG. 25 is a perspective view of an embodiment of the base unit with which a container may interface according to the invention.

FIG. 25 is a perspective view of an embodiment of the base (2500) with which any of the containers depicted in FIGS. 21 to 24 can interface according to the invention. The base includes a mating component (2502) to interface with a double check valve present on the bottom of a container. A control button display pad (2504) is illustrated on a forward-facing portion of the base, which is accessible to a user. The control button display pad may include any number of controls or display windows. Such controls or display windows may include but are not limited to an on/off button, a program selection button, a "ready" light to indicate to a user when the liquid in a container has been adequately processed, or any type of read-out display that will advise a user of an appropriate message. One skilled in the art could easily determine other types of controls or display windows to include on the pad. In this embodiment, the processing components are sized to be housed within the base in a compact manner that allows for counter-top placement or installation of the unit. However, it is to be understood that the components need not be housed within a base per se, for example, in scaled-up systems that represent permanent installations.

Another example of a container that can be used according to an embodiment of the present invention is a container that is for subsequent use with a floor cleaner, which sanitizing container can be used with the base unit of FIG. 25 according to an embodiment of the present invention. Many simple mechanical household floor cleaners, such as the Swiffer® WetJet® floor cleaner use an attachment or container for holding a detergent-based cleaner, and/or uses scrubbing strips, a cleaning pad, or the like to perform the sanitizing action separate from the liquid being used to clean floors. Embodiments of the present invention provide a container for mating with a floor cleaner, the container also for use with a base unit for providing ozonated water as a cleaning fluid. Not only is the use of such a sanitizing container more cost-effective since detergent does not need to be purchased and pads and strips do not need to be replaced. The container according to an embodiment of the present invention can be adapted for use with many different types of floor cleaning devices: Users can place regular tap water into the sanitizing container, have the water ozonated by placing the container on the base unit sanitizing system, and create their own floor cleaning fluid.

In addition to the containers described in relation to FIGS. 21-24, there are other attachments, or sanitizing containers, that can be used according to embodiments of the present invention. These sanitizing containers are for sanitizing items, and are for use with a sanitizing base unit, such as the base unit of FIG. 25. The sanitizing container comprises an outer container having a fluid transfer valve, or fluid transmission port, for removable fluid communication with the sanitizing base unit. The sanitizing container also comprises an item container for mating with the outer container, for receiving items to be sanitized. The sanitization can be achieved using a base unit that uses any number of purification or sanitization technologies, as have been described above, and as are known to those of ordinary skill in the art.

Similarly, there is provided according to an embodiment of the present invention an item sanitizing system, including a sanitizing container as described above. Specifically, the sanitizing system comprises a sanitizing container having a fluid transfer port and having an item container for holding items in the sanitizing container. The sanitizing system also includes a base for receiving the sanitizing container in removable fluid communication with the fluid transfer port, the base comprising a purification technology for purification of water received from the sanitizing container, and a water circulator for circulating water between the sanitizing container and the purification technology.

Figure 26:
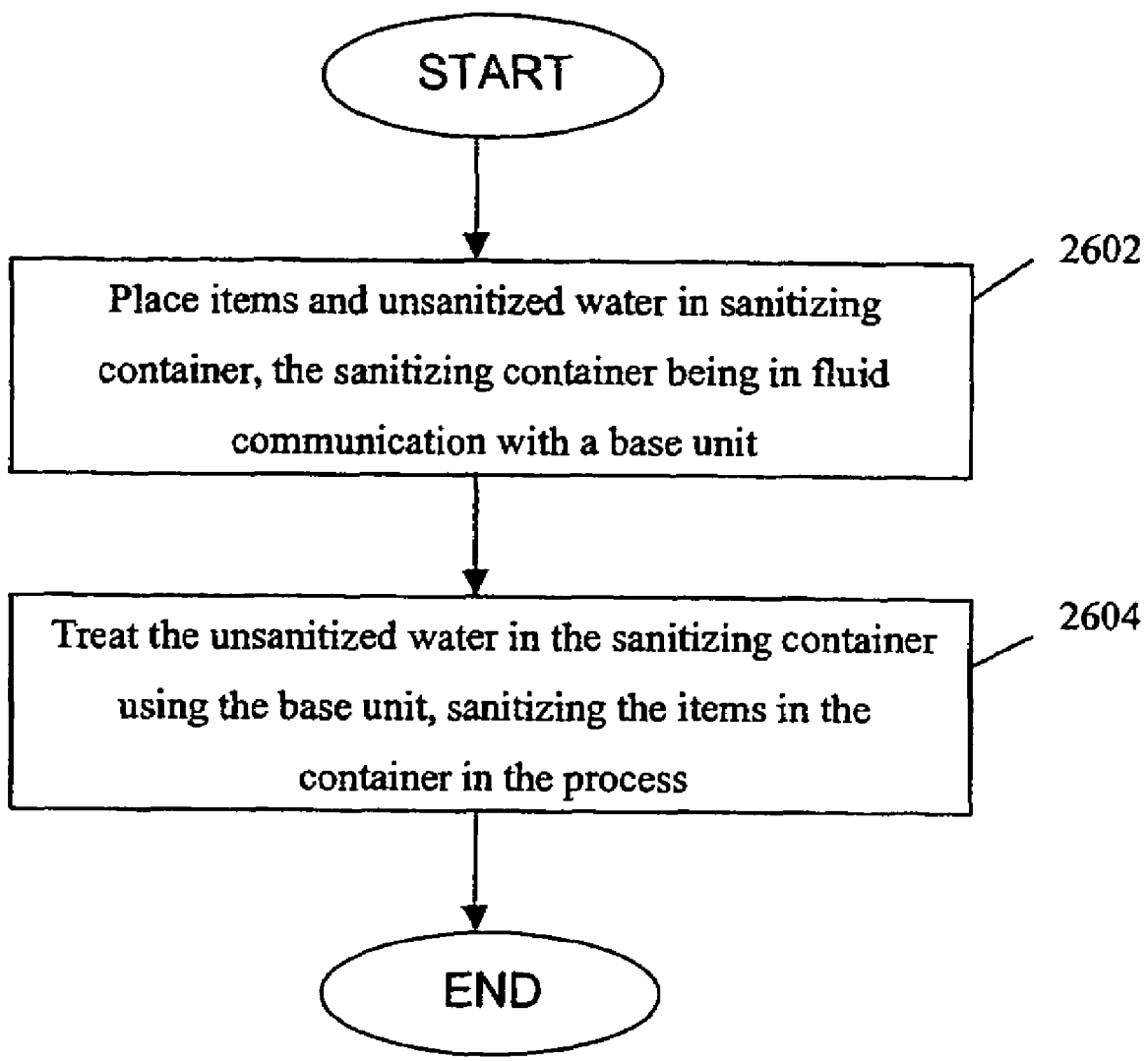
FIG. 26 is a flowchart illustrating a method of sanitizing items according to an embodiment of the present invention.

FIG. 26 is a flowchart illustrating a method of sanitizing items according to an embodiment of the present invention. Essentially, the method covers any method of using treated water, such as ozonated water or any type of purified or sanitized water, to sanitize items that have been placed in a sanitizing container such as those used in conjunction with embodiments of the present invention. The method includes the steps of: (2602) placing the items and unsanitized water in a sanitizing container, the sanitizing container being in removable fluid communication with the sanitizing base unit; and (2604) treating, or ozonating, the unsanitized water, the step of treating including sanitizing the items as the water is being treated.

It is to be understood that the step of treatment can include any of the purification steps currently available in the prior art, such as ozonation, ultra-violet irradiation, and cell membrane electrofragmentation. In particular, the step of treating can include: (a) drawing water from the container via a pump in the base unit; b) pumping water from (a) through the purification technology in the base unit; and c) directing water from (b) back into the container. Of course, when used with sanitizing containers according to embodiments of the present invention, the method can also include safely removing the sanitized items from the sanitizing container, in such a way as minimizes contamination during removal. This may depend on precautions taken by the user, but the structures used in the sanitizing containers according to embodiments of the present invention facilitate the ability to safely remove the items while reducing contamination, at least to the "operational" or functional parts of the items that are being treated or sanitized.

In this method, electronic controls such as control electronics within the base can incorporate an auto-sensing circuit to perform the step of detecting the presence of the water container on the base, and activating an appropriate program based on whether the container is detected as being present or absent. A user can activate the purification technology by pressing a button.

Regardless of the selected purification technology, the system pumps water through the purification means, and water is then is directed back into the lower reservoir. The cycle may be allowed to continue until a predetermined time or purity is reached. A light and/or audible alarm can be employed to perform a step of indicating to a user when the purification process is complete, and that the container can be removed.

Figure 27:
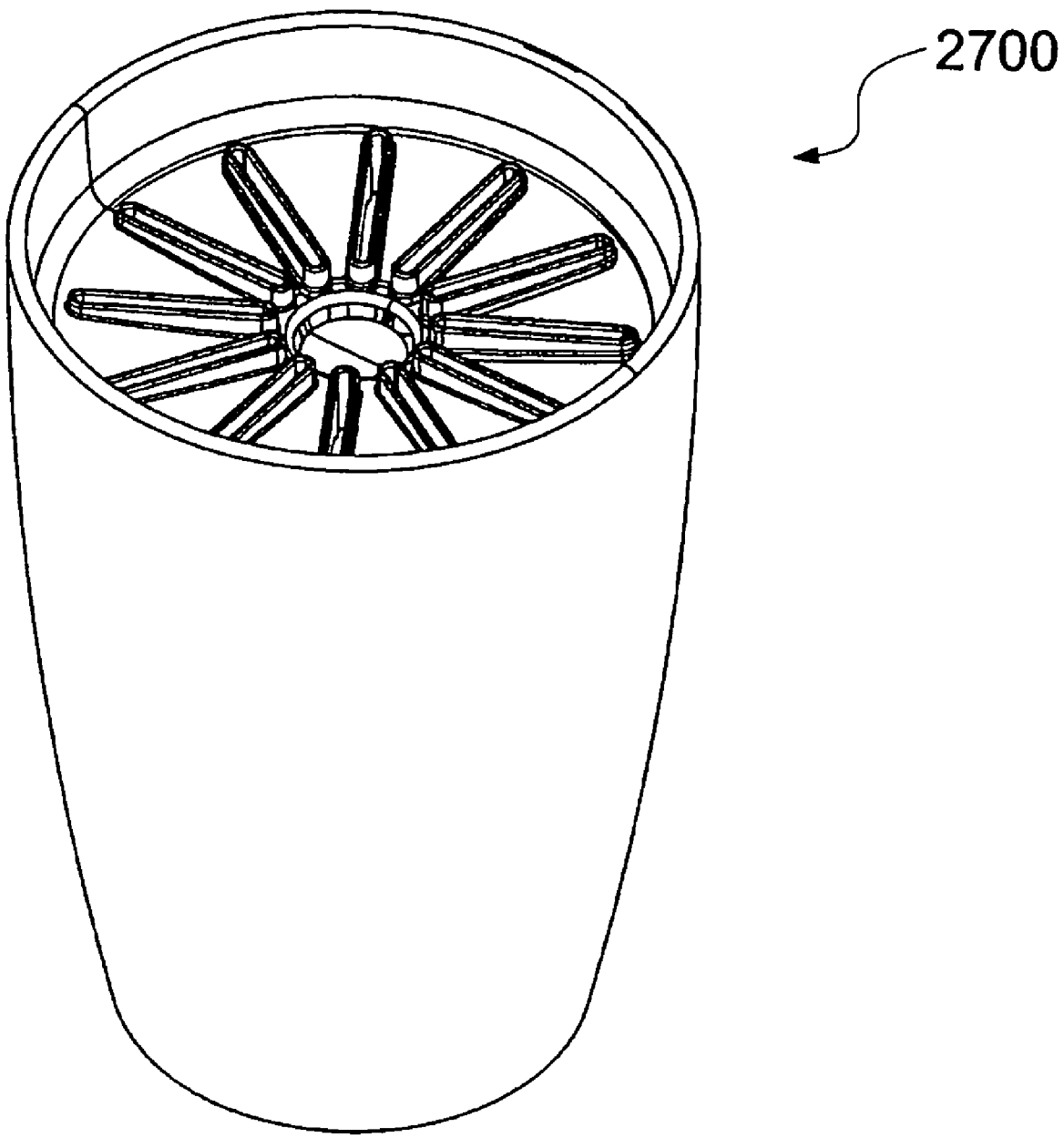
FIG. 27 illustrates a sanitizing container according to an embodiment of the present invention for sanitizing knives, which can be used with the base unit of FIG. 25.

FIG. 27 illustrates an sanitizing container (2700) for sanitizing knives according to an embodiment of the present invention that can be used with the base unit of FIG. 25. The sanitizing container (2700) can include an outer container, and an upper tray for mating with the outer container, the upper tray for receiving knives to be sanitized.

Figure 28:
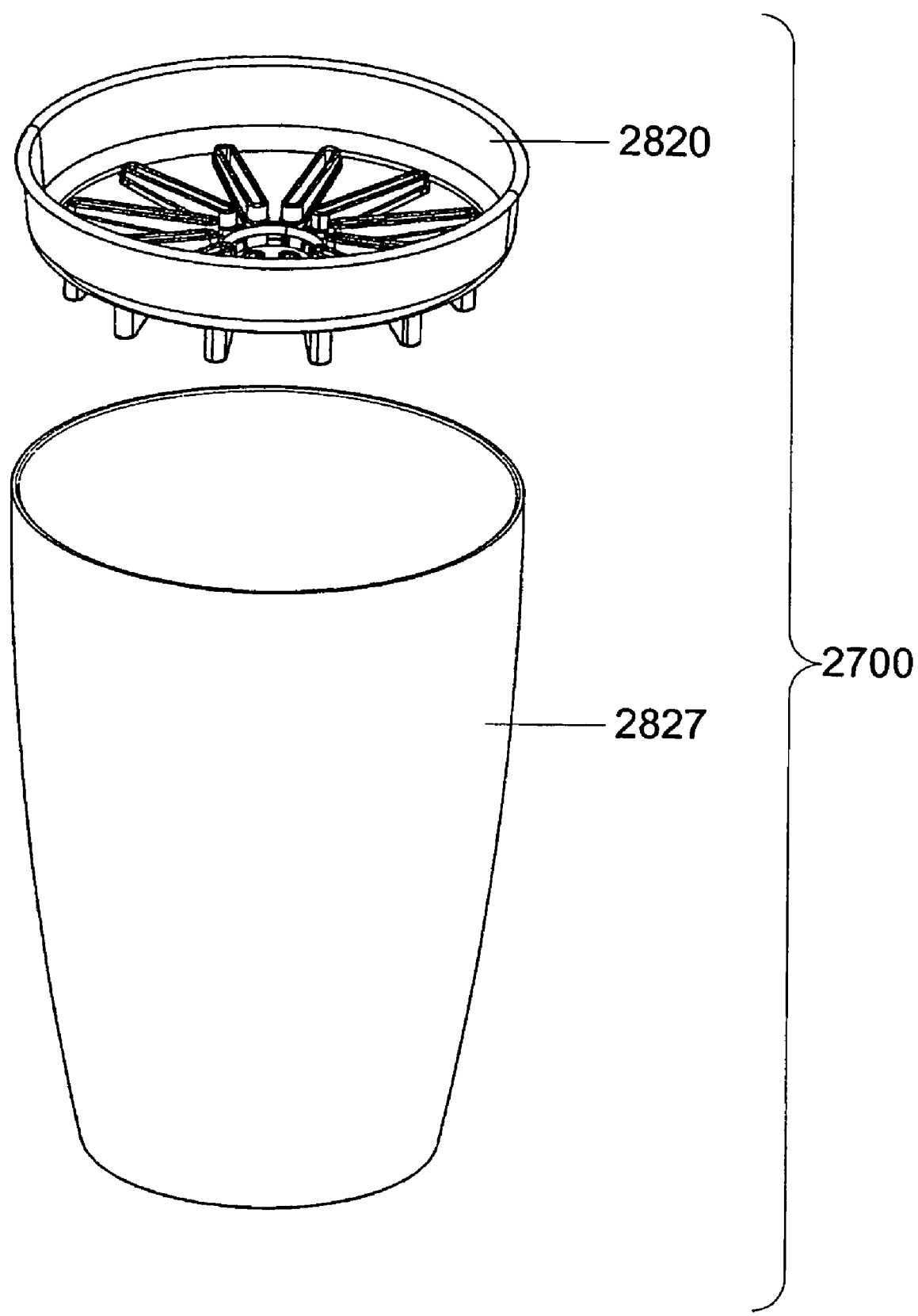
FIG. 28 illustrates an exploded view of the sanitizing container of FIG. 27.

FIG. 28 illustrates an exploded view of the sanitizing container of FIG. 27. The sanitizing container (2700) can comprise an outer container (2810) having an open top and a closed bottom, the outer container preferably being substantially cylindrical, optionally being tapered towards either the bottom or the top. The sanitizing container can also comprise an upper tray (2820), for mating with the open top of the outer container. A particular embodiment of the upper tray (2820) is shown as having a sidewall for mating with the inside of the outer container, and a lip for mating with the top of the outer container. A base of the upper tray is also shown as being provided near and joined with the bottom of the sidewall of the upper tray. The base of the upper tray defines and/or includes a plurality of knife receiving means. It is to be understood that many different embodiments and structures of an upper tray are possible, other than the one shown in FIG. 28.

Each of the knife receiving means can include a knife receiving structure, which defines a knife receiving slot. Although the knife receiving structures are shown in FIG. 28 to be substantially similar in size and in a particular configuration, it is to be understood that the knife receiving structures can be arranged in any shape or manner. In fact, a plurality of interchangeable upper trays can be provided, each upper tray having knife receiving means shaped and constructed so as to receive various types and sizes of knives. Also, although the knife receiving structures are shown in FIG. 28 to extend above and below the surface of the upper tray, it is to be understood that this is only an embodiment, and the knife receiving structures can be flush with the top and/or the bottom of the upper tray.

Figure 29:
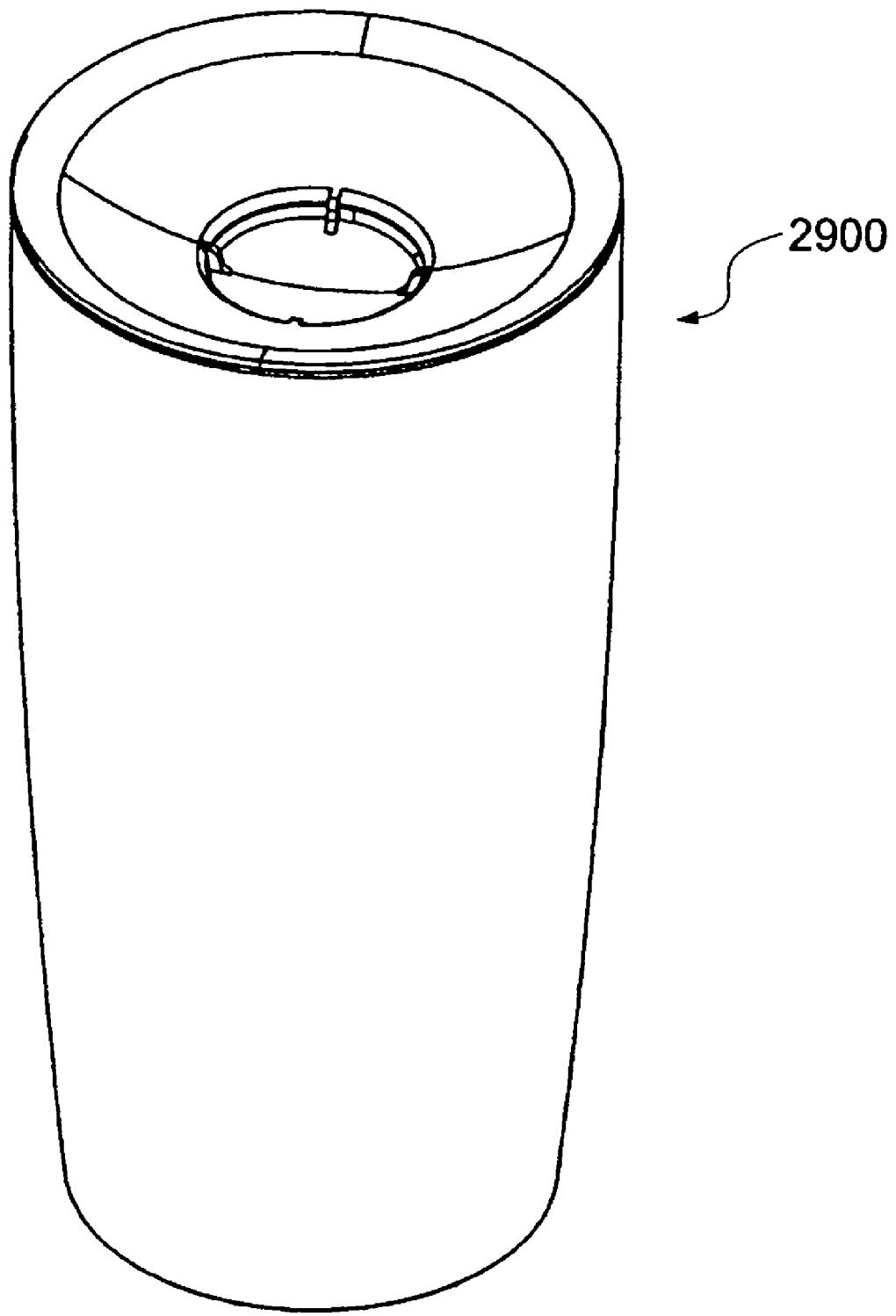
FIG. 29 illustrates an attachment for sanitizing toothbrushes according to an embodiment of the present invention, which can be used with the base unit of FIG. 25.

FIG. 29 illustrates an sanitizing container for sanitizing toothbrushes that can be used with the base unit of FIG. 25 according to an embodiment of the present invention. The sanitizing container (2900) can include an outer container, a center structure for mating with the outer container, the center structure for receiving toothbrushes to be sanitized, and a lower tray for receiving ends of the toothbrushes to be sanitized.

Figure 30:
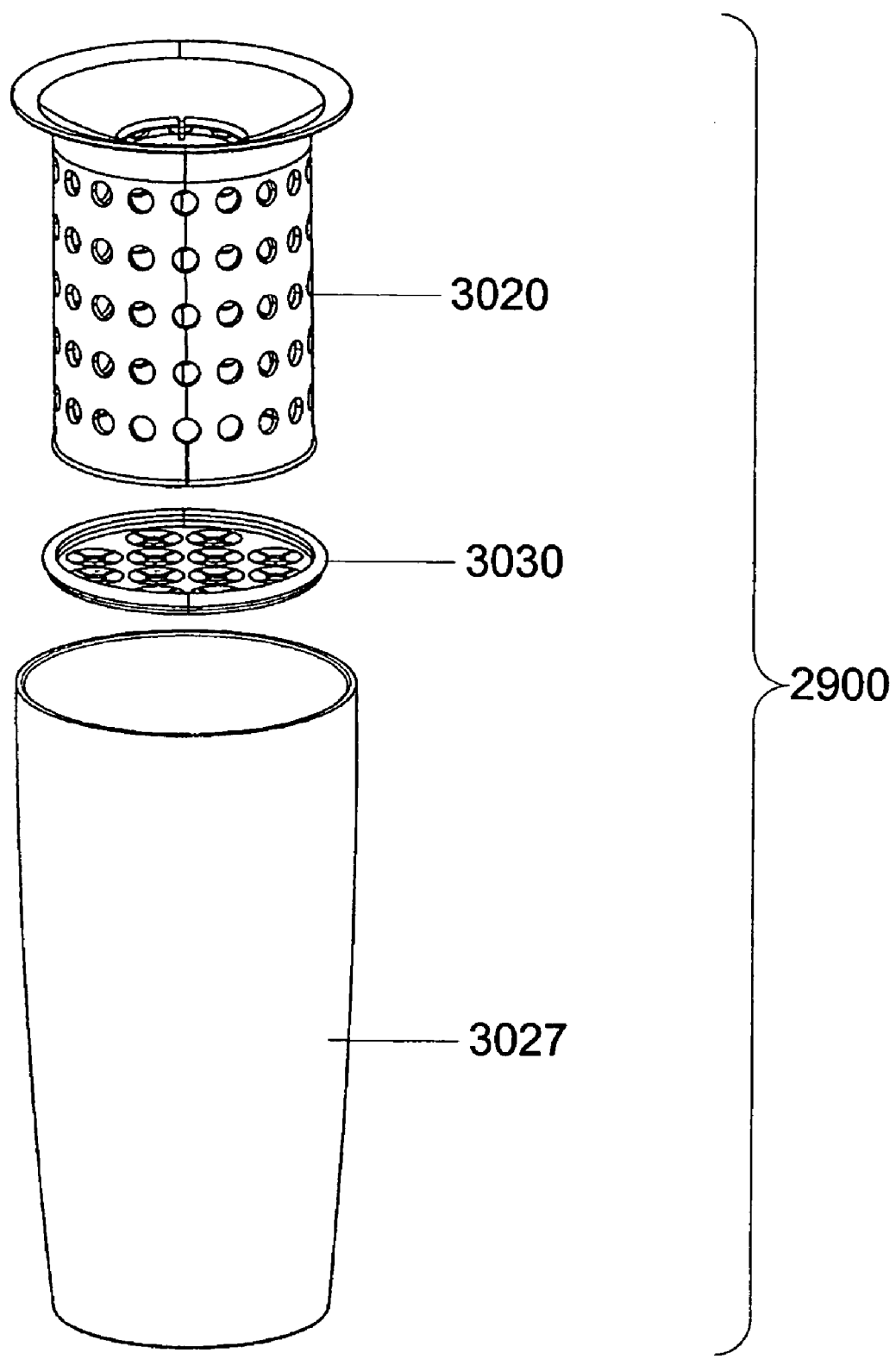
FIG. 30 illustrates an exploded view of the sanitizing container of FIG. 29.

FIG. 30 illustrates an exploded view of the sanitizing container of FIG. 29. The sanitizing container (2900) can comprise an outer container (3010) having an open top and a closed bottom, the outer container preferably being substantially cylindrical, optionally being tapered towards either the bottom or the top. The sanitizing container can also comprise a center structure (3020), for mating with the open top of the outer container. The center structure can have a cylindrical shape, with a sidewall, an open top and a closed base. A particular embodiment of the center structure is shown as having a top portion joined to the top of the sidewall, the top portion including an upper lip for mating with the top of the outer container. The top portion defines at least one opening for ends of the toothbrushes (such as the handle, or the end not having the bristles) from which to protrude. The top portion can preferably include a tapered portion extending from the upper lip, the lower end of the tapered portion defining the opening. A sidewall of the center structure preferably defines a plurality of openings for ozonated water to flow through.

A lower tray (3030) is also shown as being provided for mating with the bottom of the center structure, and for receiving ends of the toothbrushes (such as the working end, or the end having the bristles) to be sanitized. In use, the lower tray can be seated flush with the bottom of the outer container, or can be sized to be seated near the bottom of the outer container. In either case, the bottom tray keeps the toothbrushes from having direct contact with the bottom of the outer container. This is advantageous when a fluid control valve is provided in the base of the outer container, to ensure that the toothbrushes do not interfere with the flow of water into and out of the sanitizing container. It is to be understood that many different embodiments and structures of the sanitizing container are possible, other than the one shown in FIG. 30.

Figure 31:
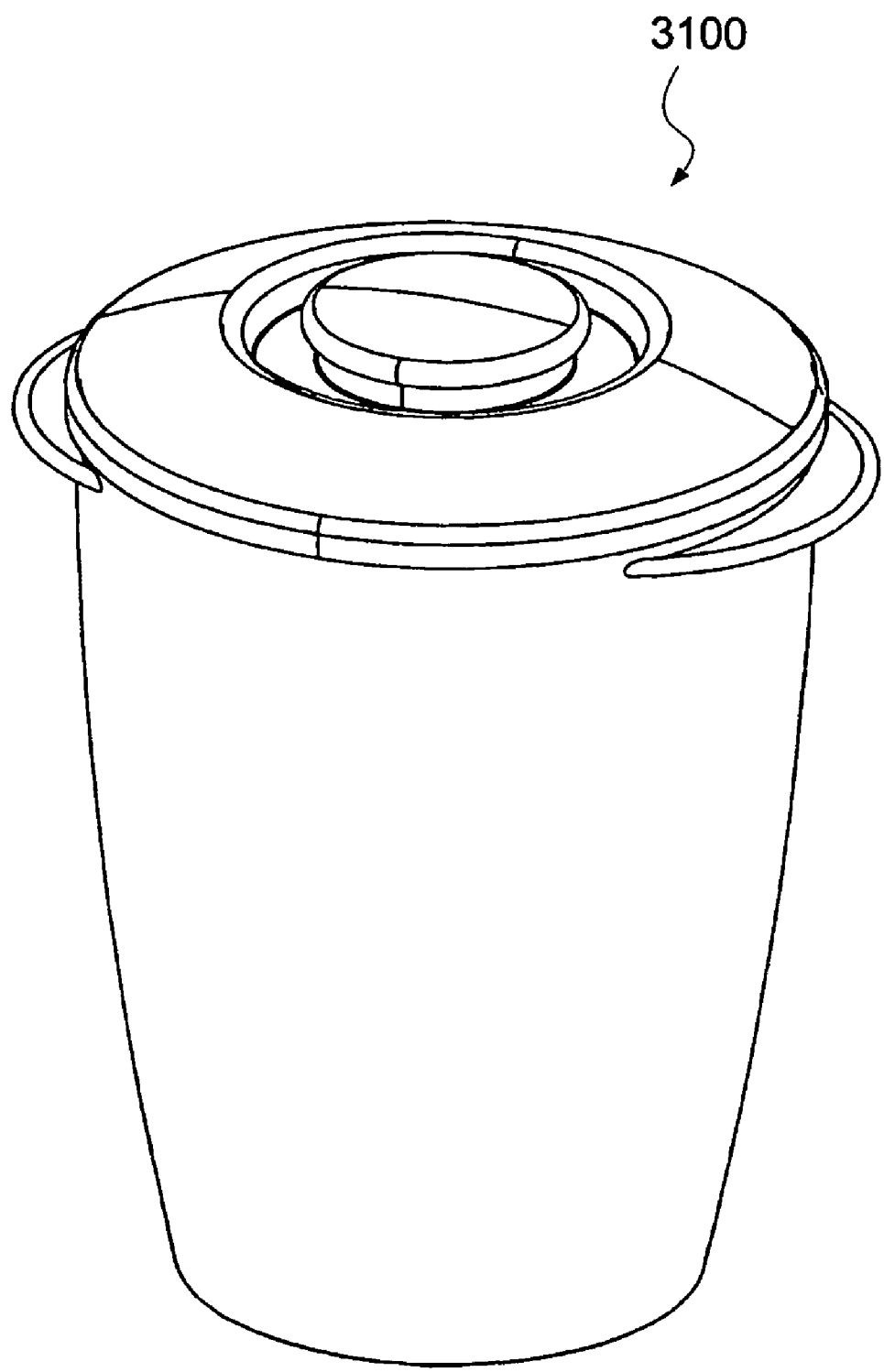
FIG. 31 illustrates an attachment for sanitizing baby bottles according to an embodiment of the present invention, which can be used with the base unit of FIG. 25.

FIG. 31 illustrates an sanitizing container for sanitizing baby bottles that can be used with the base unit of FIG. 25 according to an embodiment of the present invention. The sanitizing container (3100) can include an outer container, a center portion for mating with the outer container, the center portion for receiving baby bottles to be sanitized, and optionally includes a top cover.

Figure 32:
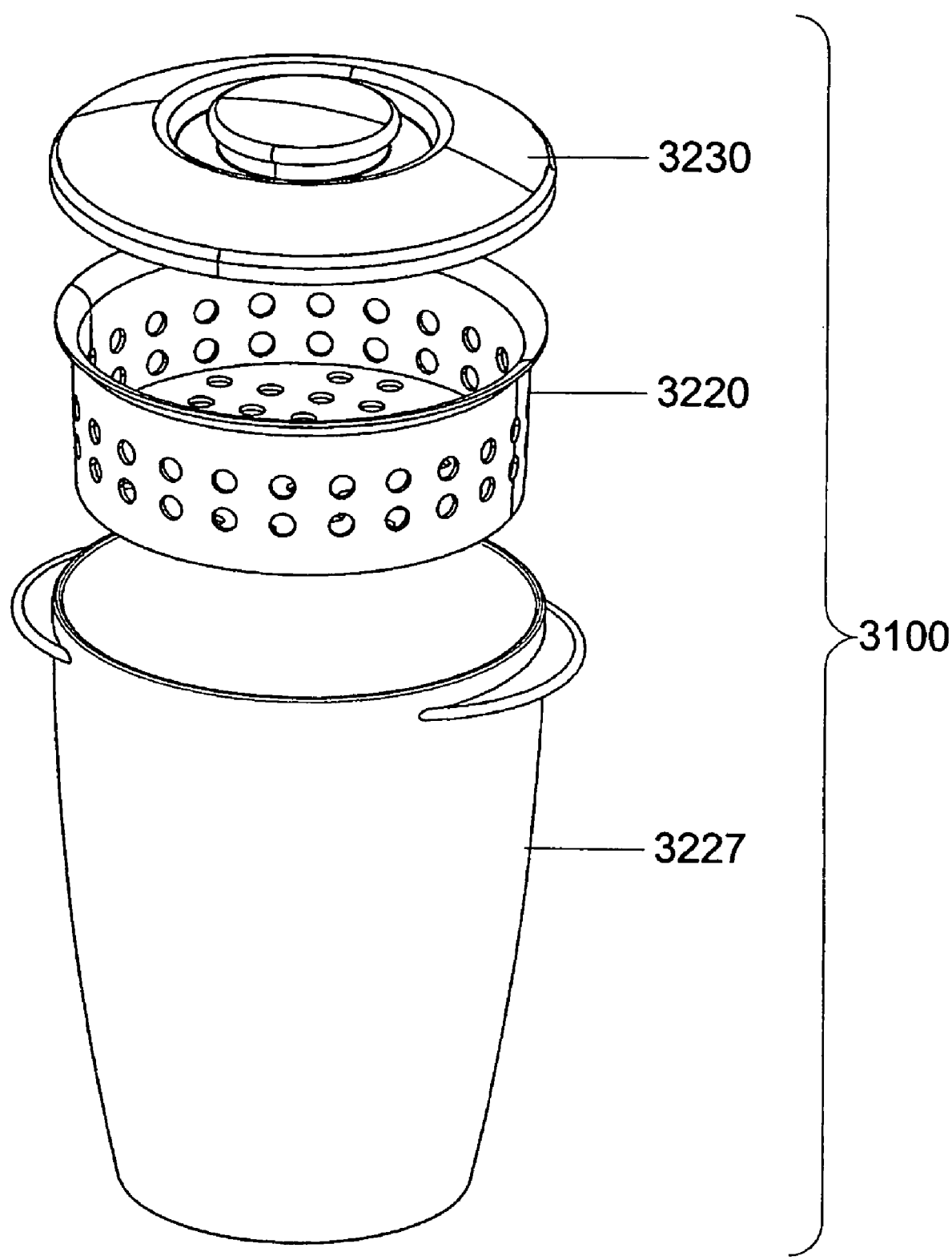
FIG. 32 illustrates an exploded view of the sanitizing container of FIG. 31.

FIG. 32 illustrates an exploded view of the sanitizing container of FIG. 31. The sanitizing container (3100) can comprise an outer container (3210) having an open top and a closed bottom, the outer container preferably being substantially cylindrical, optionally being tapered towards either the bottom or the top. The sanitizing container can also comprise a center structure (3220), for mating with the open top of the outer container. The center structure can have a cylindrical shape, with a sidewall, an open top and a closed base. A particular embodiment of the center structure is shown as having an upper lip joined to the top of the sidewall, the upper lip for mating with the top of the outer container. The top portion defines an opening through which baby bottles can be inserted and removed. The sidewall of the center structure preferably defines a plurality of openings for ozonated water to flow through. The base of the center structure can also define a plurality of openings for ozonated water to flow through. An optional top cover (3230) can be provided, for mating with the upper lip of the sidewall of the center structure. The top cover preferably includes a handle for easy removal and placement of the top cover on the sanitizing container. The top cover helps to maintain a sanitary environment by closing the top to from the surrounding environment.

It is to be understood that many different embodiments and structures of an upper tray are possible, other than the one shown in FIG. 32. For example, the sanitizing container can include a plurality of baby bottle receiving structures. These structures can be integral with the center structure, or can be provided as a separate insert. The baby bottle receiving structures are for receiving baby bottles and keeping them in a position suitable for sanitization and can be cylindrical, conical, or any other suitable shape. The baby bottle receiving structures can also be arranged so as to maximize the use of space in the sanitizing container, and allow a large number of baby bottles to be sanitized at the same time.

Of course, although a particular embodiment has been described with respect to FIGS. 31 and 32 relating to the sanitization of baby bottles, it is obvious to one of ordinary skill in the art that the open space provided in the center structure can be used for the sanitization of any number of different types of items. For example, infant pacifiers and the like could easily be sanitized in the sanitizing container of FIG. 32. In fact, baby bottles or other items could be sanitized in a lower portion of the sanitizing container, while other items are sanitized in the center structure. Moreover, the fact that the base of the center structure is preferably closer to the top of the outer container than at its bottom allows for the easy insertion and removal of the items, without having to dip one's hands in the ozonated water itself. The sanitization base with which these sanitizing containers can be used can be provided in such a way as to ensure that ozonated water will flow into the center structure and sanitize the items contained therein, without requiring the outer container to be completely full of water.

It is also to be understood that many different types of items can be sanitized simultaneously, and each container can be employed for sanitizing any number of different types of items than those with which they have been specifically described herein, either simultaneously or separately. Also, embodiments of the present invention can be adapted to provide larger containers and therefore the ability to sanitize larger items and/or greater quantities of items, for example for industrial applications.

Another advantageous application of the sanitizing containers according to embodiments of the present invention is the use of an sanitizing container for sanitizing surgical/dental equipment that can be used with the base unit of FIG. 25 according to an embodiment of the present invention. It is well known that dentists, doctors, surgeons and other medical professionals require sanitized equipment, and an effective yet simple and relatively inexpensive solution is provided by embodiments of the present invention. As has been described above, an sanitizing container can be provided having an outer container, and some sort of inner structure for receiving the medical (surgical, dental, etc.) equipment. The inner structure can be a flat tray such as described in relation to FIG. 32, or it can include a specialized item container such as described in relation to FIGS. 28 and 30. For example, an upper tray can be provided, the upper tray defining a plurality of medical equipment receiving means. The medical equipment receiving means can be shaped and constructed so as to receive various types and sizes of medical equipment, and can extend above and below the surface of the upper tray, or be flush with the top and/or the bottom of the upper tray. Such a system allows for sanitization of medical equipment directly in a dentist's or doctor's office, operating theatre, or any other local environment, without having to send the equipment to an external site to be sanitized. The turn-around time for sanitizing medical equipment can thus be significantly reduced.

Of course, a sanitizing container for sanitizing medical equipment according to an embodiment of the present invention can be produced using any type of material, such as a plastic or a metal, in order to satisfy health requirements, but also to satisfy any aesthetic preferences of doctors and dentists, who may prefer sanitizing containers that are not made of plastic, or prefer that they do not look as if they are intended for household use. For example, an inner portion of such a sanitizing container can be made of plastic, while an outer portion of the sanitizing container can be made of a more aesthetically pleasing material, such as titanium, high quality wood, and the like. It is to be understood that any number of suitable materials can be used for construction of the sanitizing container and its constituent parts. Similar materials could be used for the casing of the base. The purification technology, controls and other components typically housed within the base could alternatively be built in to a sanitizing station on a countertop in a medical facility or office, or any other alternative installation where the components are used in perhaps a different physical implementation.

Although embodiments of the present invention describe the use of these sanitizing containers with a base system that sanitizes using ozonated water, it is to be understood that the sanitizing containers are independent of the type of sanitization used. As such, these sanitizing containers can be used with any type of sanitization or purification system as described herein or as known to those of ordinary skill in the art, and any physical modifications that would be necessary would be obvious to one of ordinary skill in the art.

Figure 33:
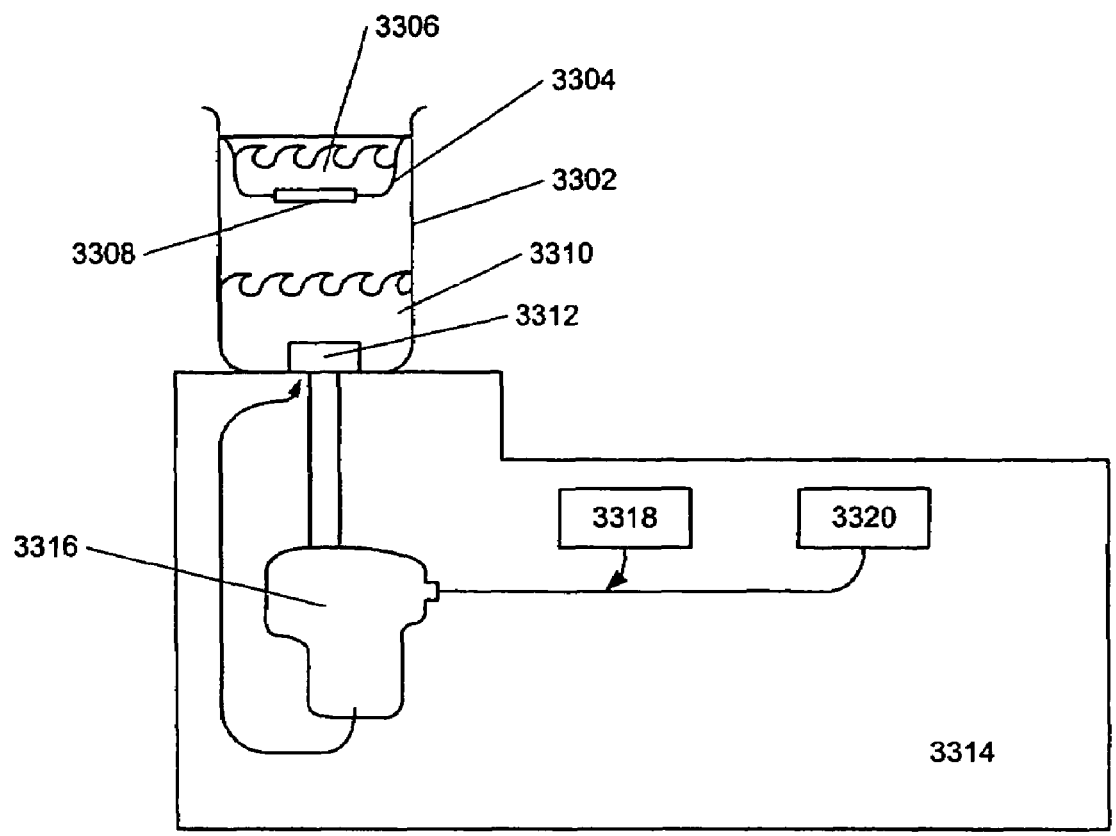
FIG. 33 is a schematic representation of an embodiment of the system incorporating a pour-through type filtration unit.

FIG. 33 is a schematic representation of an embodiment of the system incorporating a pour-through type filtration unit. In this embodiment, a removable container (3302) includes an upper reservoir (3304) containing unfiltered water (3306). The unfiltered water filters through a filter (3308), such as an extruded carbon filter between fabric. Water passing therethrough lands in the filtered water reservoir (3310), which interfaces with the double check valve (3329), in the bottom thereof. This container sits on a base (3331) housing a vortex-venturi (3316), a pump (3318), and an ozone generator (3320).

Figure 34:
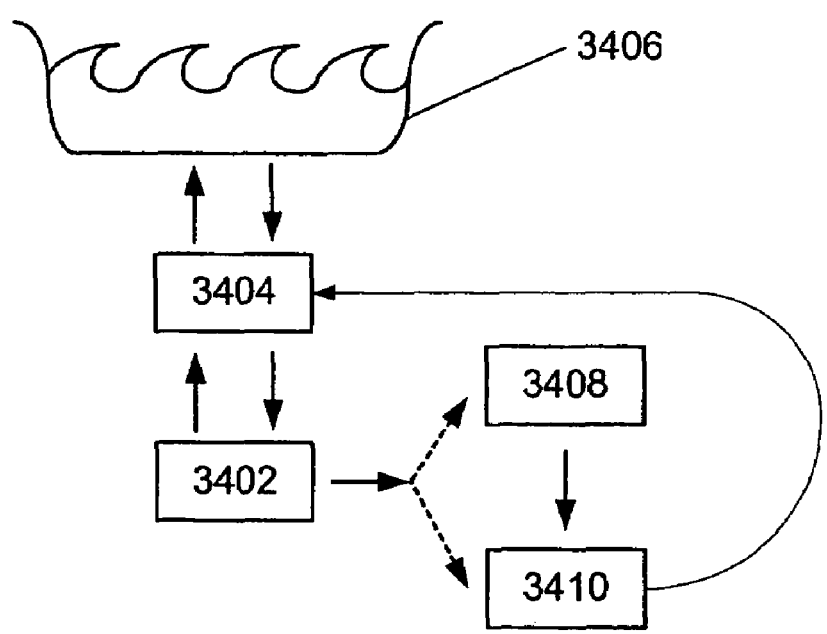
FIG. 34 is a schematic representation of an embodiment of the system according to the invention.

FIG. 34 is a schematic view of an embodiment of the invention. A sanitization system producing ozonated liquid, according to this embodiment comprises a pump (3402) for circulating liquid through the system; a double check valve (3404) for interfacing with a liquid source (3406) to be ozonated, allowing simultaneous flow into and out of the system; an ozone generator (3408) for forming ozone to be incorporated into the liquid, and a vortex-venturi (3410) for incorporating ozone into liquid. As described in more detail elsewhere, the vortex-venturi comprising an interior chamber with a central longitudinal axis into which a liquid enters in a direction tangential to the longitudinal axis, the interior chamber of the vortex-venturi having a widened initial section, an narrowed waist section with ozone entry ports formed therein, and a widened mixed fluid outlet section from which ozonated liquid is released. The ozone generator is in fluid communication with the vortex-venturi to provide ozone to the ozone entry ports.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A sanitization system for producing ozonated liquid, the system comprising:
    a pump for circulating liquid through the system;
    a fluid transfer valve for interfacing with a liquid source to be ozonated, allowing simultaneous flow into and out of the system;
    an ozone generator for forming ozone to be incorporated into the liquid; and
    a vortex-venturi for incorporating ozone into the liquid by providing accelerated entry of liquid into the vortex-venturi prior to mixing with the ozone, the vortex-venturi comprising:
        an annular interior chamber with a central longitudinal axis, the annular interior chamber of the vortex-venturi having a widened initial section, a narrowed waist section with ozone entry ports positioned therein, and a widened mixed fluid outlet section from which ozonated liquid is released; and
        a liquid inlet positioned tangential to the widened initial section of the annular interior chamber for tangential entry of the liquid into the annular interior chamber;
    the tangential entry of the liquid inducing a vortex flow of the liquid within the annular interior chamber, the vortex flow having a center of rotation, and a low pressure zone being located in the center of rotation;
    the ozone generator being in fluid communication with the vortex-venturi to provide ozone to the ozone entry ports positioned in the narrowed waist section of the annular interior chamber providing the ozone to the liquid in the low pressure zone.

2. The system according to claim 1, wherein the liquid source is contained within a container, the container being in fluid communication with the pump through the fluid transfer valve.

3. The system of claim 2, wherein a plurality of removable containers having fluid transfer valves disposed therein are used interchangeably.

4. The system of claim 2 wherein the pump, the ozone generator, and the vortex-venturi are disposed within a base.

5. The system according to claim 4, wherein the container is a removable container, the fluid transfer valve being incorporated into the removable container, and liquid is circulated into and out of the container through the fluid transfer valve, the fluid transfer valve allowing the container to be removed from the base while preventing the liquid from leaking from the container when the container is not in place.

6. The system of claim 1 wherein the ozone generator comprises a corona discharge ozone generator.

7. The system according to claim 6, wherein the corona discharge ozone generator creates ozone using a high voltage/high frequency power supply, said corona discharge ozone generator comprising:
    an ozone generating chamber having open ends, and a high voltage electrode at each of the open ends;
    insulating end caps disposed at terminal ends of the chamber, the caps having gas ports formed therein in a direction tangential to the chamber, allowing for vortex flow through the generator; and
    a ground electrode comprising a metallic foil adhered to a dielectric material.

8. The system according to claim 1 additionally comprising an oxidation reduction potential (ORP) sensor in fluid communication with the system for detecting ozone level in the fluid.

9. The system according to claim 1, additionally comprising a gas-liquid separator downstream of the vortex-venturi for separating undissolved gasses from the ozonated liquid.

10. The system according to claim 9 additionally comprising an ozone destructor downstream of and in fluid communication with the gas-liquid separator, for destroying undissolved ozone gas arising from the gas-liquid separator.

11. The system according to claim 9, wherein the gas-liquid separator separates undissolved ozone gas using centrifugal force, the separator comprising:
    an inlet through which a gas-liquid mixture arising from the vortex-venturi enters under pressure;
    a channel following from the inlet;
    means to force the gas-liquid mixture under pressure into a vortex within the channel so as to generate a centrifugal force to move undissolved ozone gas to the center of the channel and liquid to the perimeter of the channel;
    a slot positioned around the inside of the channel through which a portion of the liquid is drawn off;
    an annular chamber in communication with the slot through which the liquid passes; and
    a gas release valve comprising a gas release port within the channel through which gas exits the channel.

12. The system according to claim 11 additionally comprising a float for interacting with liquid in the chamber to close the gas release port when the liquid level is high.

13. The system according to claim 1, additionally comprising a capacitor-coupled detector of high voltage and high frequency power supply to verify the supply of power to the ozone generator, the capacitor-coupled detector comprising:
    a first wire contacting a high voltage/high frequency lead to the ozone generator;
    a second wire in close proximity to the high voltage/high frequency lead to the ozone generator, capacitance being formed due to close proximity of the first wire and the second wire; and
    a detection circuit in communication with the second wire, for detecting the capacitance comprising a microprocessor and a monostable, to verify a supply of power to the ozone generator.

14. The system according to claim 13 wherein said detection circuit is powered by an external power source or through said capacitance.

15. The system according to claim 1 additionally comprising an oxidation reduction potential sensor comprising:
a reference electrode made from silver or plated silver;
an ORP sensing electrode made from platinum, plated platinum, gold or plated gold;
an ORP sensor in fluid contact with the water path; and
a continuously monitoring sensor that controls the process time.

16. The system according to claim 1 additionally comprising a pour-through filtration unit.

17. The system according to claim 1 wherein the fluid transfer valve is a check valve.

18. The system according to claim 1 wherein the fluid transfer valve is a double check valve.

19. The system according to claim 4, wherein the container is a removable container, the removable container comprises the fluid transfer valve, and liquid is circulated into and out of the container through the fluid transfer valve, the fluid transfer valve allowing the container to be removed from an interface with the base and preventing the liquid from leaking from either the base or the container when the container is not in place.

20. A vortex-venturi for incorporating a gas into a liquid, comprising:
a cylindrical body with an annular interior chamber, a liquid inlet, a gas inlet, and a gas-liquid mixture outlet, the annular interior chamber having a helical path between the liquid inlet and the gas-liquid outlet;
the annular interior chamber comprising a widened initial section decreasing in diameter to form a narrowed waist section of a substantially cylindrical configuration, and a widened outlet section expanding to an increasing diameter relative to the narrowed waist section, the narrowed waist section having gas entry ports positioned therein;
wherein the liquid inlet is positioned tangential to the widened initial section;
wherein the tangential entry of the liquid induces a vortex flow of the liquid within the annular interior chamber, the vortex flow having a center of rotation, and a low pressure zone being located in the center of rotation; and
wherein the gas enters the annular interior chamber through the gas entry ports positioned in the narrowed waist section, the gas entry ports providing the gas to the liquid in the low pressure zone.

21. The vortex-venturi of claim 20, having one or more vanes formed in the annular interior chamber on a surface of the widened outlet section.

* * * * *